United States Patent
Denison et al.

(10) Patent No.: US 8,936,630 B2
(45) Date of Patent: Jan. 20, 2015

(54) OPTICAL STIMULATION THERAPY

(75) Inventors: Timothy J. Denison, Minneapolis, MN (US); Kunal Paralikar, Minneapolis, MN (US); Gordon O. Munns, Stacy, MN (US); Wesley A. Santa, Andover, MN (US); Peng Cong, Plymouth, MN (US); Christian S. Nielsen, River Falls, WI (US); John D. Norton, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 229 days.

(21) Appl. No.: 12/951,766

(22) Filed: Nov. 22, 2010

(65) Prior Publication Data

US 2011/0125077 A1    May 26, 2011

Related U.S. Application Data

(60) Provisional application No. 61/264,550, filed on Nov. 25, 2009, provisional application No. 61/301,836, filed on Feb. 5, 2010.

(51) Int. Cl.
*A61N 5/06* (2006.01)
*A61B 17/00* (2006.01)
(Continued)

(52) U.S. Cl.
CPC ............ *A61N 5/0601* (2013.01); *A61N 5/0622* (2013.01); *A61B 2017/00084* (2013.01);
(Continued)

(58) Field of Classification Search
USPC ................................ 607/88, 92, 96, 100, 102
See application file for complete search history.

(56) References Cited

U.S. PATENT DOCUMENTS

| 4,671,285 A | 6/1987 | Walker |
| 4,711,251 A | 12/1987 | Stokes |

(Continued)

FOREIGN PATENT DOCUMENTS

| DE | 102009025407 A1 | 12/2010 |
| WO | 2006055582 A2 | 5/2006 |

(Continued)

OTHER PUBLICATIONS

Denison et al., "A 2 µW 100 nV/rtHz Chopper-Stabilized Instrumentation Amplifier for Chronic Measurement of Neural Field Potentials," IEEE Journal of Solid-State Circuits, vol. 42, pp. 2934-2945 (Dec. 2007).

(Continued)

*Primary Examiner* — William Thomson
*Assistant Examiner* — John R Downey
(74) *Attorney, Agent, or Firm* — Shumaker & Sieffert, P.A.

(57) ABSTRACT

Methods of delivering optical stimulation to a target tissue from an optical stimulation device are provided. One method comprises sensing a temperature at the optical stimulation device or proximate to the optical stimulation device, and adjusting the delivery of light to the target tissue based on the sensed temperature. Another method comprises delivering the light to the target tissue with an optical light guide and sensing bioelectric signals with a sense electrode, wherein the optical light guide and the sense electrode each comprise a material that produces substantially no induced current in an electromagnetic field. Another method comprises delivering light from a light source of an optical stimulation device to a window of the optical stimulation device, delivering the light from the window to an optical light guide optically connected to the window, and delivering the light to a target tissue via the optical light guide.

23 Claims, 17 Drawing Sheets

(51) Int. Cl.
*A61M 5/142* (2006.01)
*A61N 1/365* (2006.01)
*A61N 1/08* (2006.01)
*A61B 18/00* (2006.01)

(52) U.S. Cl.
CPC ............ *A61M5/14276* (2013.01); *A61N 1/365* (2013.01); *A61N 2001/086* (2013.01); *A61N 2005/063* (2013.01); *A61N 2005/0651* (2013.01); *A61B 2018/00839* (2013.01); *A61N 2005/0612* (2013.01)
USPC ............................................. 607/92; 607/88

(56) References Cited

U.S. PATENT DOCUMENTS

| | | | |
|---|---|---|---|
| 4,951,672 | A | 8/1990 | Buchwald et al. |
| 4,966,144 | A | 10/1990 | Rochkind et al. |
| 5,409,482 | A | 4/1995 | Diamantopoulos |
| 5,872,879 | A | 2/1999 | Hamm |
| 5,902,326 | A | 5/1999 | Lessar et al. |
| 6,494,900 | B1 | 12/2002 | Salansky et al. |
| 6,832,115 | B2 | 12/2004 | Borkan |
| 6,921,413 | B2 | 7/2005 | Mahadevan-Jansen et al. |
| 7,190,993 | B2 | 3/2007 | Sharma et al. |
| 7,280,870 | B2 | 10/2007 | Nurmikko et al. |
| 7,288,108 | B2 | 10/2007 | DiMauro et al. |
| 7,349,618 | B2 | 3/2008 | Nielsen et al. |
| 7,736,301 | B1 | 6/2010 | Webler et al. |
| 7,883,536 | B1* | 2/2011 | Bendett et al. ................ 607/89 |
| 8,285,381 | B2* | 10/2012 | Fahey ............................ 607/48 |
| 8,355,793 | B2* | 1/2013 | Dadd et al. .................... 607/57 |
| 2003/0191500 | A1 | 10/2003 | Stokes et al. |
| 2004/0101514 | A1 | 5/2004 | Liu et al. |
| 2004/0146245 | A1* | 7/2004 | Harwit ........................... 385/38 |
| 2005/0027191 | A1 | 2/2005 | Uutela et al. |
| 2005/0070987 | A1 | 3/2005 | Erickson |
| 2006/0015146 | A1 | 1/2006 | Girouard et al. |
| 2006/0049957 | A1* | 3/2006 | Surgenor et al. ......... 340/825.19 |
| 2006/0058627 | A1* | 3/2006 | Flaherty et al. ............... 600/409 |
| 2006/0247509 | A1 | 11/2006 | Tuccillo et al. |
| 2007/0053996 | A1 | 3/2007 | Boyden et al. |
| 2007/0054319 | A1 | 3/2007 | Boyden et al. |
| 2007/0100232 | A1 | 5/2007 | Hiller et al. |
| 2007/0213783 | A1 | 9/2007 | Pless |
| 2007/0225674 | A1 | 9/2007 | Molnar et al. |
| 2007/0244524 | A1 | 10/2007 | Qu et al. |
| 2007/0261127 | A1 | 11/2007 | Boyden et al. |
| 2008/0039709 | A1* | 2/2008 | Karmarkar ................... 600/410 |
| 2008/0077190 | A1 | 3/2008 | Kane et al. |
| 2008/0085265 | A1 | 4/2008 | Schneider et al. |
| 2008/0102119 | A1 | 5/2008 | Grovender et al. |
| 2008/0180278 | A1 | 7/2008 | Denison |
| 2008/0269841 | A1 | 10/2008 | Grevious et al. |
| 2009/0054954 | A1 | 2/2009 | Foley et al. |
| 2009/0054955 | A1 | 2/2009 | Kopell et al. |
| 2009/0082691 | A1 | 3/2009 | Denison et al. |
| 2009/0088680 | A1 | 4/2009 | Aravanis et al. |
| 2009/0093403 | A1 | 4/2009 | Zhang et al. |
| 2009/0099038 | A1 | 4/2009 | Deisseroth et al. |
| 2009/0099627 | A1 | 4/2009 | Molnar et al. |
| 2009/0118800 | A1 | 5/2009 | Deisseroth et al. |
| 2009/0192558 | A1 | 7/2009 | Whitehurst et al. |
| 2009/0281528 | A1 | 11/2009 | Grovender et al. |
| 2010/0099965 | A1 | 4/2010 | Jacobson et al. |
| 2010/0114275 | A1* | 5/2010 | Min ............................ 607/116 |
| 2010/0161017 | A1 | 6/2010 | Choi et al. |
| 2010/0174329 | A1 | 7/2010 | Dadd et al. |
| 2010/0190229 | A1* | 7/2010 | Zhang et al. .............. 435/173.1 |
| 2010/0262212 | A1 | 10/2010 | Shoham |
| 2010/0286626 | A1* | 11/2010 | Petersen et al. ............... 604/264 |
| 2010/0324631 | A1 | 12/2010 | Tass et al. |

FOREIGN PATENT DOCUMENTS

| | | |
|---|---|---|
| WO | WO 2006/055582 | 5/2006 |
| WO | 2008029001 A1 | 3/2008 |
| WO | WO 2008/061135 | 5/2008 |
| WO | 2008089003 A2 | 7/2008 |
| WO | 2009155371 A1 | 12/2009 |
| WO | 2011/066320 A2 | 6/2011 |

OTHER PUBLICATIONS

Berndt et al., "Bi-stable neural state switches," *Nature Neuroscience*, vol. 12, pp. 229-234 (2008).

Han X. et al., "Multiple-Color Optical Activation, Silencing, and Desynchronization of Neural Activity, with Single-Spike Temporal Resolution," PLoS ONE, 2(3):e299, http://www.plosone.org/article/info:doi/10.1371/journal.pone.0000299 (2007).

Yan et. al., "Cloning and Characterization of Human $\beta,\beta$-Carotene-15,15'-Dioxygenase That is Highly Expressed in the Retinal Pigment Epithelium," Genomics 72 (2), pp. 193-202 (2001).

Dittgen et. al., "Lentivirus-based genetic manipulations of cortical neurons and their optical and electrophysiological monitoring in vivo," Proc. Natl. Acad. Sci. USA, vol. 101, No. 52, pp. 18206-18211 (Dec. 28, 2004).

Nagel, et al., "Channelrhodopsin-2, a directly light-gated cation-selective membrane channel," Proc. Natl. Acad. Sci. USA, vol. 100, No. 24, pp. 13940-13945 (Nov. 25, 2003).

Huang et al., "Plasmonic Photothermal Therapy (PPTT) Using Gold Nanoparticles," Lasers Med Sci, 23, pp. 217-228 (2008).

Invitation to Pay Additional Fees dated Apr. 12, 2011 for corresponding PCT Application PCT/US2010/057878 (6 pgs.).

International Search Report and Written Opinion dated Jun. 7, 2011 for corresponding PCT Application PCT/US2010/057878 (21 pgs.).

Office action from U.S. Appl. No. 12/951,852, dated Aug. 8, 2013, 11 pp.

Final Office Action from U.S. Appl. No. 12/951,852, dated Feb. 26, 2014, 13 pp.

Response to Office Action dated Aug. 8, 2013, from U.S. Appl. No. 12/951,852, filed Nov. 8, 2013, 14 pp.

Response to Office Action dated Feb. 26, 2014 from U.S. Appl. No. 12/951,852, filed Jun. 26, 2014, 9 pp.

Office Action from U.S. Appl. No. 12/951,852, dated Jul. 22, 2014, 10 pp.

Response to Office Action dated Jul. 22, 2014, from U.S. Appl. No. 12/951,852, filed Oct. 22, 2014, 11 pp.

* cited by examiner

OPTICAL STIMULATION THERAPY

This application claims the benefit of U.S. Provisional Application No. 61/264,550, filed Nov. 25, 2009 and of U.S. Provisional Application No. 61/301,836, filed Feb. 5, 2010, both assigned to the assignee of this application, the entire disclosures of both of which are incorporated herein by reference.

STATEMENT REGARDING SEQUENCE LISTING

The Sequence Listing in accordance with 37 C.F.R. §§1.821-1.824 associated with this application is provided in text format in lieu of a paper copy, and is hereby incorporated by reference into the specification in its entirety. The name of the text file containing the Sequence Listing is "SEQUENCELISTING.txt." The text file is 18 KB, was created on Feb. 5, 2010, and is being submitted electronically via EFS-Web.

TECHNICAL FIELD

The disclosure relates to optical stimulation therapy.

BACKGROUND

Electrical stimulation of neural tissue serves as the core of many neurological therapies, and can provide relief for a variety of disorders, improving the quality of life for many patients. In some cases, electrical stimulation may be characterized by a lack of specificity in the excitation of neural tissue. In particular, it can be difficult to stimulate a specific, localized neural population due to constraints on electrode geometry and placement. For example, the area of stimulation may be dictated by electrode size, which can be generally orders of magnitude greater than the cellular targets of interest. In some cases, this may lead to overexciting cellular networks and or inefficient stimulation, and may result in stimulation of non-target cells. In addition, inhibitory stimuli through the use of electrical coupling generally may be accomplished only through a electrical stimulation block that involves inefficient, high frequency stimulation, thereby limiting the therapy modulation strategy in some circumstances. The presence of electrodes in tissue may also place limitations on electromagnetic exposure from electromagnetic sources such as magnetic resonance imaging (MRI) and electrosurgery devices. In addition, electrical stimulation can undermine the ability to sense underlying electrical neural activity simultaneously with delivery of electrical stimulation. In particular, electrical stimulation currents flowing through the tissue that are necessary to achieve a localized current density high enough to depolarize the cell or axon can mask the bioelectrical activity to be sensed.

SUMMARY

In general, the disclosure describes devices for delivering optical stimulation and techniques for delivering optical stimulation to neural tissue from an optical stimulation device. The optical stimulation device, in some examples, may deliver optical stimulation configured to support optogenetic neuromodulation. For optogenetic neuromodulation, cellular control and interfacing is achieved by activating light-sensitive channel proteins, also referred to as opsins that are embedded in desired neuronal populations. Opsins are expressed on the neuronal membrane by lentiviral or retroviral-based delivery of their genes, allowing for direct cellular targeting through genetic mechanisms.

As examples, two microbial opsins, Channelrhodopsin-2 (cation channel activated by ~450 nm light) and Halorhodopsin (chloride pump activated by ~580 nm light) may be suitable for optogenetic stimulation, as they provide a mechanism to modulate neural information flow by respectively exciting and inhibiting action potentials in neural networks. Although these opsins are described for purposes of illustration, an optical stimulation device may be configured to deliver optical stimulation for use with other suitable opsins. Accordingly, the description of particular opsins should not be considered limiting of the techniques broadly described in this disclosure.

In one aspect, the present disclosure is directed to a method for delivering optical stimulation, the method comprising delivering light to a target tissue via an optical stimulation device, sensing a temperature at the optical stimulation device or proximate to the optical stimulation device, and adjusting the delivery of light to the target tissue based on the sensed temperature.

In another aspect, the present disclosure is directed to an implantable medical system comprising a therapy delivery module comprising a light source and a controller that controls the light source to generate light, an optical light guide configured to transmit the light from the light source to a target tissue, and a temperature sensor configured to sense a temperature proximate the therapy delivery module, wherein the therapy delivery module is configured to adjust the delivery of light to the target tissue based on a temperature sensed by the temperature sensor.

In another aspect, the present disclosure is directed to a method for delivering optical stimulation, the method comprising delivering light from an optical stimulation device to a target tissue via an optical light guide, wherein the optical stimulation device is remote from the target tissue, and sensing bioelectric signals with a sense electrode, wherein the optical light guide and the sense electrode each comprise a material that produces substantially no induced current in an electromagnetic field.

In another aspect, the present disclosure is directed to an implantable medical system comprising an implantable optical stimulation device comprising a light source that generates light and a sense circuit, an optical light guide configured to transmit the light from the light source to a target tissue, wherein the optical light guide comprises a non-galvanic material, wherein the implantable optical stimulation device is implantable remotely from the target tissue, and a sense electrode implantable proximate the target tissue to sense electrical signals, wherein the sense electrode comprises a material that produces substantially no induced current in an electromagnetic field.

In another aspect, the present disclosure is directed to a method for delivering optical stimulation, the method comprising delivering light from a light source of an optical stimulation device to a window of the optical stimulation device, delivering the light from the window to an optical light guide optically connected to the window, and delivering the light to a target tissue via the optical light guide.

In another aspect, the present disclosure is directed to an implantable medical system comprising, an implantable medical device comprising a light source and a window, and an optical light guide configured to transmit light to a target tissue, wherein the optical light guide is optically connected to the window so that light is delivered from the optical stimulation device to the optical light guide through the window.

The details of one or more examples of the disclosure are set forth in the accompanying drawings and the description below. Other features, objects, and advantages will be apparent from the description and drawings, and from the claims.

DETAILED DESCRIPTION

Figure 1:
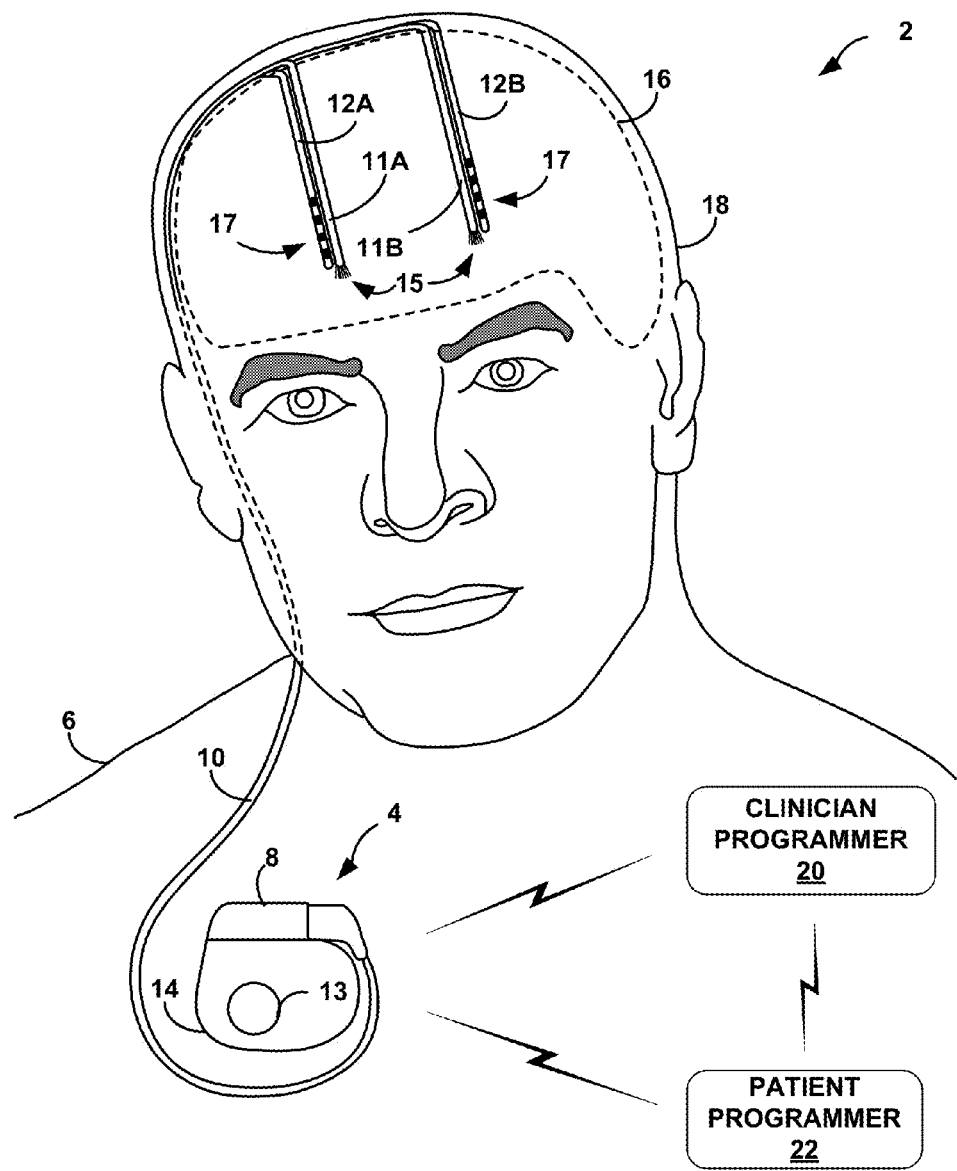
FIG. 1 is a conceptual diagram illustrating an example therapy system that includes an implantable stimulator coupled to one or more optical fibers for optical stimulation and one or more sense electrodes.

The disclosure, in some examples, describes optical stimulation techniques, such as optogenetic stimulation techniques. The techniques may be capable of exciting or inhibiting neural activity in target neuron populations. For optogenetic stimulation, the target neurons may be selectively transfected with genes that express opsins that are activated by light emitted into the target tissue. The light may be selected to activate an opsin to initiate neuronal spikes or to deactivate or inhibit an opsin to cease or prevent neuronal spikes. The light may also be selected to activate an opsin to suppress a neuronal spike. An optogenetic stimulation system may be configured as an implantable medical device that can deliver optical stimulation through implantable optical fibers or other light-delivery apparatus to a target tissue, such as to specific or highly specific neuron populations. The high degree of specificity provided by the optical stimulation may limit or prevent stimulation of non-target tissue, possibly reducing side effects of stimulation.

As non-limiting examples, the optical stimulation may be delivered to target tissue within the brain or spinal cord of a human patient. However, the disclosure is not so limited. Rather, optical stimulation may be delivered to any of a variety of target tissue sites to support any of a variety or therapies. A few examples include without limitation cardiac tissue to support cardiac therapy such as pacing, cardioversion, defibrillation, resynchronization, or other therapies, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, or the like.

In one example, the optogenetic stimulation system may also include a therapeutic agent delivery system, such as a pump, to deliver a therapeutic agent capable of transfecting the target neurons with the genes to express the opsins described above, such as a liquid gene therapy agent including a lentiviral or retroviral vector for transfecting the target neurons. The therapeutic agent delivery system may provide regular, irregular, programmed, or clinician-activated doses of the therapeutic agent to the target neurons to ensure that the target neurons continue to express the desired opsins. In another example, the optogenetic stimulation system may also include sensing electrodes that sense electrical signals within the patient, such as to provide a closed-feedback loop for the control of the optical stimulation provided by the optogenetic stimulation system.

The optogenetic system may be fully implantable in the patient. In other examples, some portions of the optogenetic stimulation system may be implantable in the patient, while other components are configured to be external to the patient. For example, one or more programmers may be external to the patient, and communicate with an implanted stimulation device via wireless telemetry. In other cases, a stimulation generator may be external to the body, and be configured to deliver light, receive sensed signals, and/or deliver fluid via percutaneously implanted optical delivery elements (such as optical fibers), leads and/or conduits. Optical fibers will be described for purposes of illustration, but without limitation as the use of other types of optical delivery elements. In some cases, optical fibers, electrical leads, or fluid delivery conduits may be constructed as separate elements, or two or more of such components combined with one another in a lead or other elongated element.

FIG. 1 is a conceptual diagram illustrating an example system 2 that may be used to deliver stimulation therapy to patient 6. Patient 6 ordinarily, but not necessarily, will be a human. Generally, therapy system 2 includes an implantable stimulator 4 that delivers optical stimulation, such as light 15, to patient 6 via one or more implantable optical fibers 11. The terms "light" or "optical light" as used herein refer to electromagnetic radiation having a wavelength and intensity that has a physiologically measurable effect and may include visible light, infrared light, and ultraviolet light. In some examples, light that may be used to provide the optical stimulation of system 2 may include visible light having a wavelength of between about 380 nm and about 750 nm, infrared light having a wavelength of between about 700 nm and about 300 μm, and ultraviolet light having a wavelength between about 10 nm and about 400 nm. For example, a first optical fiber 11A may deliver visible light having a certain wavelength and intensity, and a second optical fiber 11B may deliver visible light having the same wavelength and intensity, or a different wavelength at the same intensity, or the same wavelength and a different intensity, or the second optical fiber 11B may deliver non-visible light, such as infrared or ultraviolet light. The fibers 11A and 11B may be coupled to the same light source or different light sources. In some cases, a single light source may be optically multiplexed across the fibers 11A, 11B to deliver light via the different fibers at different times. In some examples, the light source may deliver light via both fibers 11A, 11B simultaneously. The light delivered via one optical fiber 11A may be the same as the light delivered via another optical fiber 11B, e.g., in terms of characteristics or parameters such as wavelength, amplitude, pulse width or pulse rate. Alternatively, the light delivered via the optical fibers 11A, 11B may have different characteristics or parameters.

The implantable optical fibers 11A, 11B may be deployed to a target site as part of one or more bundles of optical fibers, such as implantable optical fiber bundle 10, or separately. In some cases, stereotactic or other positioning techniques may be used to precisely position the optical fibers with respect to target tissue sites. If only one optical fiber 11 is implanted, instead of multiple fibers, then fiber bundle 10 and the single optical fiber 11 may be one and the same. The optical stimulation may be in the form of optical light of a particular wavelength and may be delivered as pulses, e.g., with a defined pulse width and pulse rate. Various parameters of the pulses may be defined by a stimulation program. The pulses may be delivered substantially continuously for a relatively long period of time, such as several seconds or more, or in pulse bursts, segments, or patterns, and may be delivered alone or in combination with pulses defined by one or more other stimulation programs. Although FIG. 1 shows a fully implantable stimulator 4, techniques described in this disclosure may be applied to external stimulators having optical fibers deployed via percutaneously implantable leads. In addition, in some examples, system 2 may include sense electrodes deployed within patient 6, such as implantable sense electrodes 17 implanted on leads 12A and 12B alongside optical fibers 11 and/or a sense electrode located on a housing 14, i.e., "can" or "case," of the implantable stimulator 4. Leads 12A, 12B may be implanted side-by-side with optical fibers 11A, 11B, respectively, and fastened or formed together. In other examples, leads and associated sense electrodes may be formed in a common lead body with one or more optical fibers, such as a conductor and one or more electrodes placed on a lead sheath that covers an optical fiber. In some examples, an electrical conductor and optical fiber can run axially along the lead, while in another example an electrical conductor may be wound in a coil that runs along the lead while one or more optical fibers extend through the middle of the coil. In other examples, implantable stimulator 4 may be coupled to one or more leads which may or may not be bifurcated. In such examples, the leads may be coupled to implantable stimulator 4 via a common lead extension or via separate lead extensions. The sense electrodes may detect various types of bioelectric signals, including local field potentials, energy spectra in different bands, such as alpha, beta, or gamma bands of brain activity, and electrical signals associated with electrocorticography (ECoG) or electroencephalography (EEG). Other sensors may also be included within or on housing 14 or external to housing 14 within patient, including an accelerometer or other posture sensor and a pressure sensor. In some examples, in addition to sensing bioelectric signals or as an alternative, the sense electrodes could be selectively used to deliver electrical stimulation, such that the implantable stimulator may deliver optical stimulation and electrical stimulation on, e.g., a selective basis. For example, optical or electrical stimulation could be delivered at different times or at the same time independently of one another or on a coordinated basis.

In the example illustrated in FIG. 1, implantable stimulator 4 is implanted within a subcutaneous pocket in a clavicle region of patient 6. Optical fibers 11 may be implanted using a stylet for insertion stiffness while the optical fiber is being implanted in the target tissue. For example, the stylet may allow a surgeon to easily manipulate optical fiber 11 as it is guided from the clavical region, though the neck, into cranium 18, and into brain 16 of patient. A stylet may also be used to guide optical fibers to other target tissues and other treatments, such as peripheral nerve stimulation (PNS), peripheral nerve field stimulation (PNFS), deep brain stimulation (DBS), cortical stimulation (CS), pelvic floor stimulation, gastric stimulation, and the like. The stylet may be removable after insertion of optical fiber 11 so that the optical fiber 11 is flexible after insertion such that the stylet does not interfere with chronic treatment by the optical fiber. In one example, optical fiber 11 or the lead carrying optical fiber 11 may include a stylet lumen for receiving the stylet and for allow the removal of the stylet.

Stimulator 4 generates programmable optical stimulation, e.g., optical pulses with selected wavelengths and intensities, and delivers the stimulation via one or more implantable optical fibers 11. In some cases, the wavelengths and intensities of the optical pulses may be fixed, or limited to a narrow range. In other examples, the wavelengths and intensities of the optical pulses may be variable, i.e., tunable to produce a wider range of desired wavelengths and intensities. In some cases, multiple sets of one or more implantable optical fibers 11 may be provided. In the example of FIG. 1, two optical fibers 11A and 11B (collectively referred to as "optical fibers 11") are each carried as part of an optical fiber bundle 10 until a distal end of bundle 10 is bifurcated into separate optical fiber segments 11. Each optical fiber 11A, 11B may be a single optical fiber. Alternatively, in some examples, each optical fiber may include multiple fibers that together deliver optical stimulation. Optical fibers 11A, 11B may provide optical transmission between stimulator 4, which provides a light source for the optical stimulation, and the area of treatment, shown as the brain 16 of patient 6 in FIG. 1. Stimulator 4 provides optical stimulation by generating optical light 15 with a desired wavelength and intensity, as described in more detail below, and directing the optical light 15 into optical fiber 11 at the proximal end of the optical fiber. The optical light 15 is transmitted along optical fiber 11 until it is emitted from a distal end of optical fiber 12, as shown in FIG. 1.

Figure 8:
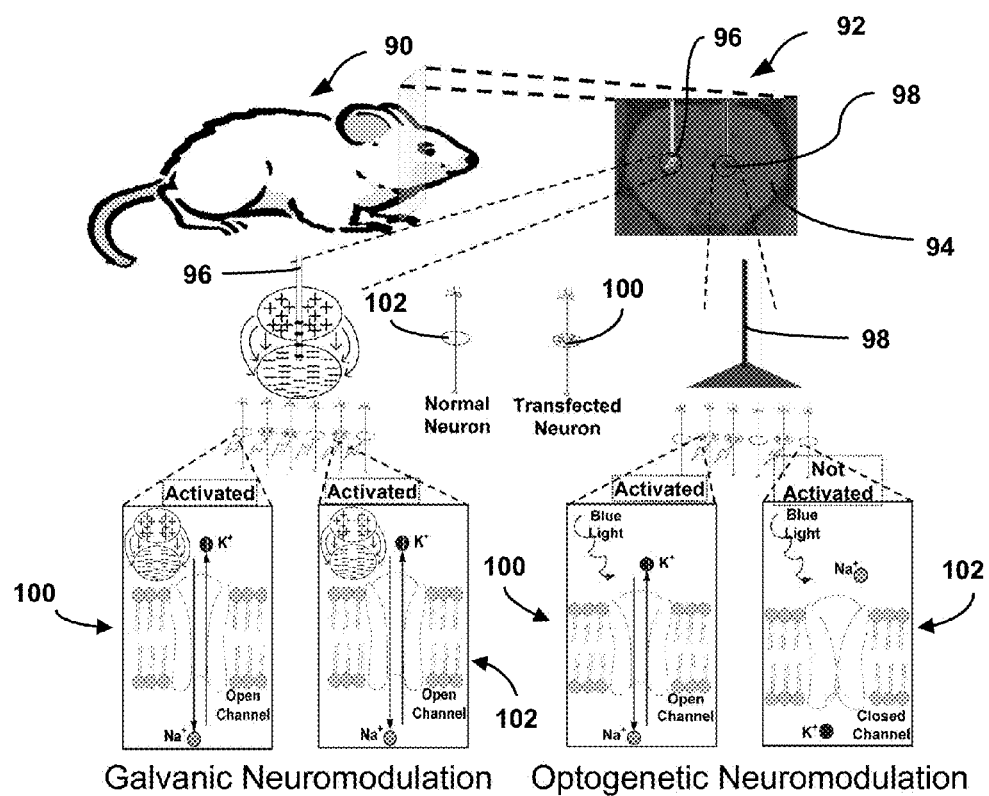
FIG. 8 is a conceptual diagram illustrating a comparison between electrical stimulation and selective optogenetic modulation of neuron cells.

Other means of light communication may be used in place of an optical fiber, including a wave guide, a hollow tube, a liquid filled tube, and a light pipe. In an alternative example, a light source, such as a light emitting diode (LED), is implanted at the target treatment site, e.g., at the distal end of a lead or on the housing of a microstimulator device implanted proximate target tissue, such that the light is emitted into the target tissue from the LED, rather than via an optical fiber. In this case, a conducting lead may be implanted to extend from an optical stimulation controller to the LED to conduct electrical energy to power the light source Optical stimulation of the target tissue may be configured to cause optogenetic modulation of a selected target population of cells, such as, for example, a particular area of neurons within the brain or spinal cord. The optogenetic modulation may activate light-sensitive channel proteins, referred to herein as "opsins," that are expressed within the target population of cells. Opsin expression may be triggered by a biological vector that introduces the opsin to the target neurons. In one example, the biological vector comprises a gene therapy agent, such as a lentivirus or retrovirus that is designed to selectively transfect a particular population of neurons to selectively deliver the genes to the target neurons that will express for the desired opsins. Optogenetic modulation may be particularly useful because the genetic modification provided by biological vectors allow a specific cell population to be targeted and transfected, without modifying neighboring cell populations so that when the area is exposed to stimulation light, only the selected and transfected cell population is actually stimulated. Thus, biological vectors, such as lentiviral-based or retroviral-based vectors, provide for delivery of their genes, allowing for direct cellular targeting through genetic mechanisms as opposed to reliance on electrode positioning. This allows the "placement" of the therapeutic stimulation to be performed by a highly selective biological vector rather than relying on a surgeon who, no matter how skilled, cannot place an electrode with the same precision. An example of this advantage is shown in FIG. 8, which compares conventional electrical stimulation of neurons, also referred to as galvanic neuromodulation, and optogenetic neuromodulation in a rodent model 90. A cross section 92 of the rodent brain 94 shows an implanted electrode 96 and an optical fiber 98 at a location where target neurons have been transfected. As can be seen on the left portion of FIG. 8, electrode 96 not only activates the target (transfected) neurons 100, but also other nearby neurons (normal neurons) 102, which are not desired to be activated. In contrast, genetic transfection coupled with optical stimulation, as shown on the right portion of FIG. 8, causes only the transfected target neurons 100 to be activated, while the non-transfected, non-target neurons 102 remain unactivated.

In one example, a first opsin may be used as an activating or exciting opsin that, when exposed to a specific wavelength of light or range of wavelengths, causes the target neuron membrane to become permeable to cations into the neuron, which depolarizes the neuron, also referred to as activating the neuron, and causes a neural spike. A second opsin may be used as an inhibiting opsin that, when exposed to a different wavelength of light or range of wavelengths, acts to hyperpolarize the neuron, also referred to as inhibiting or deactivating the neuron, to counteract the cation permeability of the target neuron. An example of a first opsin is channelrhodopsin-2 that is described in Berndt et al, "Bi-stable neural state switches," *Nature Neuroscience*, vol. 12, pp. 229-34 (2008), U.S. Published Patent Application No. US 2007/0054319 to Boyden et al., U.S. Published Patent Application No. US 2007/0053996 to Boyden et al., and U.S. Published Patent Application No. US 2007/0261127 to Boyden et al., the disclosures of which are incorporated herein by reference in their entireties, which is activated to provide a cation-permeable channel that activates the target neuron. For example, the cation-permeable channel may activate the target neuron when exposed to light having a wavelength between about 420 nm and about 500 nm, such as between about 450 nm and about 495 nm, or in one example about 470 nm, and with an intensity of between about 0.5 mW/mm$^2$ and about 10 mW/mm$^2$, such as between about 1 mW/mm$^2$ and about 5 mW/mm$^2$, and in one example about 2.4 mW/mm$^2$. In one example, a channelrhodopsin-2 opsin is activated by blue light having a wavelength of between about 450 nm and about 495 nm, such as between about 450 nm and about 470 nm. In one example, the channelrhodopsin-2 opsin may only need to be exposed to this light for a pulse of between about 1 ms and about 1 second, such as between 5 ms and about 50 ms, and in one example about 10 ms. The channelrhodopsin-2 opsin holds its activated state and slowly deactivates with a probability window of several seconds. An example channelrhodopsin-2 opsin may also be deactivated or "switched off" by illumination of a second wavelength of light. In one example, a modified channelrhodopsin-2 may be deactivated by illumination with a green light having a wavelength of between about 495 nm and about 570 nm, such as between about 510 nm and about 550 nm, and in one example about 535 nm, with an intensity of between about 0.5 mW/mm$^2$ and about 10 mW/mm$^2$, such as between about 1 mW/mm$^2$ and about 5 mW/mm$^2$, and in one example about 2.4 mW/mm$^2$, and the channelrhodopsin-2 may be exposed to a pulse of between about 20 ms and about 75 ms, such as between about 40 ms and about 60 ms, and in one example about 50 ms. An example of a second opsin is a halorhodopsin described in Han X. et al., "Multiple-Color Optical Activation, Silencing, and Desynchronization of Neural Activity, with Single-Spike Temporal Resolution," PLoS ONE, 2(3):e299, http://www-.plosone.org/article/info:doi/10.1371/journal.pone.0000299 (2007), the entire disclosure of which is incorporated herein by reference. This second opsin may be activated to provide an anion pump that inhibits or deactivates the target neuron. In one example, the second opsin is activated, thus deactivating the target neuron, when exposed to yellow light having a wavelength of between about 550 nm and about 610 nm, such as between about 570 nm and about 590 nm, and in one example about 580 nm, and with an intensity of between about 0.5 mW/mm$^2$ and about 25 mW/mm$^2$, such as between about 10 and about 21 mW/mm$^2$ in one example or between about 1 mW/mm$^2$ and about 5 mW/mm$^2$ in another example. In one example, the halorhodopsin may only need to be exposed to this light for between about 10 ms and about 1 second, such as between 20 ms and about 100 ms, and in one example about 40 ms. Not only can halorhodopsin be used to inhibit the firing of the target neurons, but it can also be used to deactivate neurons that were previously activated by the activation of the channelrhodopsin-2 described above. For example, if a 470 nm wavelength light pulse of about 10 ms activates the channelrhodopsin-2, which can remain actives for several seconds, a 535 nm wavelength light pulse may be emitted to deactivate the channelrhodposin-2, and a 580 nm wavelength light pulse may be emitted to activate the halorhodopsin and abruptly deactivate the target neurons. In one example, both the first opsin that activates the target neuron and the second opsin that inhibits the target neuron may be activated simultaneously or substantially simultaneously in order to modulate the threshold potential of the target neuron, such as for the treatment of schizophrenia.

The devices and techniques described in this disclosure may be used in conjunction with any of a variety of opsins or other materials effective in supporting excitation, inhibition or other desired effects on the target tissue. In one example, a first opsin or set of opsins, also referred to as a light-activated cation channel protein (or "LACC"), comprises the protein, or portions of the protein Channelrhodopsin-2 (ChR2). ChR2 is a rhodopsin derived from the unicellular green alga

*Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2) (Nagel, et. al. Proc. Natl. Acad. Sci. USA 100:13940, and references cited therein). The LACC protein may incorporate retinal that is added to the system, or, depending on the cell type that is used, background levels of retinal present in the cell may produce the required retinal. The use of the term "opsin" herein is intended to encompass either the opsin or the rhodopsin form of the first opsin and the second opsin. Typically, Chop2 and ChR2 can be interconverted by the addition or removal of the cofactor. Thus, as used herein, a LACC protein comprises an opsin with or without a co-factor. For example, as used herein, where a nucleic acid codes for an opsin protein such as Chop2, it codes for a light activated cation channel protein such as ChR2. Additionally, as used herein, where a cell expresses an opsin protein such as Chop2, it expresses a LACC protein.

The opsins may also cause the modulation of the flow of anions such as chloride across a membrane when activated by light. In one example, a second opsin or set of opsins, also referred to as an anion pump, may comprise the protein, or portions of the protein, halorhodopsin (NpHR). NpHR is a light-driven chloride pump rhodopsin derived from the unicellular archaeon *Natronomonas pharaonis*. Optically induced electrical and chemical changes due to activation of the opsins by light are also contemplated.

In some examples, it may desirable to add cofactor (usually in the nanomolar to micromolar range). In other examples, no addition of retinal is required. In some examples, the medium may provide the required cofactor. In one example, the opsin protein covalently binds retinal. The term retinal, as used in comprises all-trans retinal, 11-cis retinal, and other isomers of retinal.

In some examples, the protein Bcdo can be expressed along with ChR2. Bcdo converts the common dietary molecule beta carotene into retinal (Yan et. al., Genomics 72 (2): 193 (2001)), thus providing retinal to convert Chop2 to ChR2.

As used herein, the terms "ChR2," "Chop2," and "NpHR" mean the full proteins or fragments thereof. In one example, the LACC comprises the amino terminal 310 amino acids of Chop2 which is referred to herein as Chop2-310. One example comprises the amino terminal 310 amino acids of ChR2 which is referred to as ChR2-310. The amino-terminal 310 amino acids of ChR2 show homology to the 7-transmembrane structure of many microbial-type rhodopsins, and comprise a channel with a light-gated conductance. In an example, a LACC protein comprises a 7-transmembrane protein. Preferably the LACC protein is a 7-transmembrane protein that either has a binding affinity for retinal, or has retinal bound to it.

In one example, the LACC is derived from a microbial-type rhodopsin. In one example, the LACC of the present invention is derived from a bacteriorhodopsin.

In one example, each opsin is a single-component protein that is an opsin protein. As used herein, a single component protein is a single covalently linked chain of amino acids. Multiple component systems require communication between non-covalently linked molecules, which can be much slower than within-protein signaling via conformational changes. The opsin allows the creation of light-gated membrane conductance with a single protein component. While not being bound by theory, it is believed that the retinal in ChR2, as a microbial type rhodopsin, is strongly bound, allowing the retinal to re-isomerize to the all-trans ground state in a dark reaction without the need for other enzymes. This mechanism allows for fast recovery (closing of the ionic channel) when the light is removed, and it obviates the need for other enzyme components for re-generation of the all trans-retinal and closing of the channel.

In one example, the light-activated cation-channel Channelrhodopsin-2 (ChR2) is genetically introduced into a cellular membrane.

The LACC protein may also comprise the protein sequence of Chop2-310 [SEQ ID NO:1]. The anion pump protein may comprise the protein sequence of NpHR [SEQ ID NO:4]. "Protein" in this sense includes proteins, polypeptides, and peptides. Also included within the opsin protein are amino acid variants of the naturally occurring sequences, as determined herein. In one example, the variants are greater than about 75% homologous to the protein sequence of Chop2 or Chop2-310, such as greater than about 80%, for example greater than about 85%, such as greater than about 90%. In some examples, the homology will be as high as about 93 to about 95 or about 98%. In one example, the variants are greater than about 75% homologous to the protein sequence of NpHR, such as greater than about 80%, for example greater than about 85%, such as greater than about 90%. In some examples, the homology will be as high as about 93 to about 95 or about 98%. Homology in this context means sequence similarity or identity, with identity being preferred. This homology will be determined using standard techniques known in the art. The compositions of the opsins include the protein and nucleic acid sequences provided herein including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

The LACC proteins may be shorter or longer than the protein sequence of Chop2 or Chop2-310. Thus, in one example, included within the definition of LACC proteins are portions or fragments of the protein sequence of Chop2 or of Chop2-310. The anion pump proteins may be shorter or longer than the protein sequence for NpHR. Thus, in one example, included within the definition of anion pump proteins are portions or fragments of the protein sequence of NpHR. In addition, nucleic acids may be used to obtain additional coding regions, and thus additional protein sequence, using techniques known in the art.

In one example, the LACC proteins are derivative or variant protein sequences, as compared to Chop2 or Chop2-310. In one example, the anion pump proteins are derivative or variant protein sequences as compared to NpHR. That is, the derivative LACC proteins or derivative anion pump proteins may contain at least one amino acid substitution, deletion or insertion, with amino acid substitutions being particularly preferred. The amino acid substitution, insertion or deletion may occur at any residue within the LACC protein or the anion pump protein.

In one example, the LACC proteins are amino acid sequence variants of the ChR2, Chop2, ChR2-310, Chop-310 or [SEQ ID NO:1]. In another example, the anion pump proteins are amino acid sequence variants of NpHR. These variants fall into one or more of three classes: substitutional, insertional or deletional variants. These variants ordinarily are prepared by site specific mutagenesis of nucleotides in the DNA encoding the LACC proteins or anion pump proteins, using cassette or PCR mutagenesis or other techniques well known in the art, to produce DNA encoding the variant, and thereafter expressing the DNA in recombinant cell culture. Amino acid sequence variants are characterized by the predetermined nature of the variation, a feature that sets them apart from naturally occurring allelic or interspecies variation of the LACC proteins or anion pump proteins. The variants typically exhibit the same qualitative biological activity as the naturally occurring analogue, although variants can also be selected which have modified characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed breast cancer variants screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. In some examples, small alterations in the characteristics of the LACC proteins or anion pump proteins are desired, substitutions are generally made in accordance with Table 1:

| Original Residue | Exemplerary Substitution |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile, | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in Table 1. For example, substitutions may be made which more significantly affect the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants or derivatives of the LACC proteins typically exhibit the same qualitative activity as the Chop2, ChR2, Chop-310, or ChR2-310 protein, while variants or derivatives of the anion pump proteins typically exhibit the same qualitative activity as NpHR, although variants or derivatives also are selected to modify the characteristics of the opsins as needed. Variants or derivatives can show enhanced ion selectivity, stability, speed, compatibility, and reduced toxicity. For example, the protein can be modified such that it can be driven by a different wavelength of light than the wavelength of around 460 nm of the wild type ChR2 protein. The protein can be modified, for example, such that it can be driven at a higher wavelength such as about 480 nm, 490 nm, 500 nm, 510 nm, 520 nm, 530 nm, 540 nm, 550 nm, 560 nm, 570 nm, 580 nm, or 590 nm. Similarly, the anion pump protein can be modified such that it can be driven by a different wavelength of light than the 580 nm of the wild type NpHR.

The opsins may incorporate un-natural amino acids as well as natural amino acids. The unnatural amino acids can be used to enhance ion selectivity, stability, speed, compatibility, or to lower toxicity.

In one example, the opsins may comprise a fusion protein comprising a light-activated channel protein, such as a LACC protein or anion pump protein described above. It is well known in the art that fusion proteins can be made that will create a single protein with the combined activities of several proteins. In one example, the fusion proteins can be used to target Chop2, ChR2, or NpHR to specific cells or regions within cells.

In one example, a fusion protein comprising a LACC protein or anion pump protein is a fusion protein that targets sub-cellular regions of the cell. The fusion proteins may target, for instance, axons, dendrites, and synapses of neurons. In one example, a PDZ (PSD-95, Dlg and ZO-1) domain is fused to ChR2 or Chop2 which target dendrites. In another example, Axon initial segment (AIS) domain is fused to ChR2 or Chop2 which target axons.

Other fusion proteins may be used, such as are proteins combining an opsin and a fluorescent protein in order to allow for monitoring of the localization of the opsin. Example fusion proteins are those with red fluorescent protein (mCherry), yellow fluorescent protein (YFP), enhanced yellow fluorescent protein (EYFP), cyan fluorescent protein (CFP), green fluorescent protein (GFP), and woodchuck hepatitis post-transcriptional regulatory element (WPRE). These fusion proteins, such as a ChR2-mCherrry fusion protein or a NpHr-EYFP or NpHR-EYFP-WPRE fusion protein, allow for the independent stimulation of ChR2 or NpHR and the simultaneous monitoring of localization. The simultaneous stimulation and monitoring of localization can be carried out in many cell types including mammalian systems.

In one example, an opsin protein is provided that is non-toxic in the cells in which it is expressed. In one example, the opsin proteins do not perturb the basal electrical properties, alter the dynamic electrical properties, or jeopardize the prospects for cellular survival. In one example, the opsin proteins do not alter the membrane resistance of the cells in the absence of light. In one example, the opsin proteins do not lead to apoptosis in the cells, nor lead to the generation of pyknotic nuclei. In one example, in the absence of light, the presence of the opsin proteins do not alter cell health or ongoing electrical activity, at the level of subthreshold changes in voltage or in spike output, either by shunting current through leaky channels or by altering the voltage dependence of existing neuronal input-output relationships. In one example, the presence of opsin protein creates no significant long-term plastic or homeostatic alterations in the electrical properties of neurons expressing the protein.

It would be understood by a person of skill in the art that the opsin proteins can be coded for by various nucleic acids. Each amino acid in the protein is represented by one or more sets of 3 nucleic acids (codons). Since many amino acids are represented by more than one codon, there is not a unique nucleic acid sequence that codes for a given protein. It is well understood by persons of skill in the art how to make a nucleic acid that can code for the opsin proteins by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein. An example nucleic acid sequence for coding for a LACC comprises SEQ ID NO:2. An example nucleic acid sequence for coding for an anion pump protein comprises SEQ ID NO:5.

It is known by persons of skill in the art that the codon systems in different organisms can be slightly different, and that therefore where the expression of a given protein from a given organism is desired, the nucleic acid sequence can be modified for expression within that organism.

In one example, the nucleic acid sequence codes for an opsin protein that is optimized for expression with a mammalian cell. A preferred embodiment comprises a nucleic acid sequence optimized for expression in a human cell. In one example, a nucleic acid sequence that codes for a light-activated cation protein that is optimized for expression with a human cell comprises SEQ ID NO:3. In one example, a nucleic acid sequence that codes for an anion pump protein that is optimized for expression with a mammalian cell comprises SEQ ID NO:5.

In one example, reagents are provided for genetically targeted expression of the opsin proteins including ChR2 and NpHR. Genetic targeting may be used to deliver opsin proteins to specific cell types, to specific cell subtypes, to specific spatial regions within an organism, and to sub-cellular regions within a cell. Genetic targeting also relates to the control of the amount of opsin protein expressed, and the timing of the expression.

In one example, a reagent for genetically targeted expression of the opsin protein comprises a vector which contains the gene for the opsin protein. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One example vector is an episome, such as a nucleic acid molecule capable of extrachromosomal replication. Example vectors are those capable of autonomous replication and/or expression of nucleic acids to which they are linked. Vectors capable of directing the expression of genes to which they are operatively linked are referred to herein as "expression vectors". Other example vectors are viruses such as lentiviruses, retroviruses, adenoviruses and phages. In some examples, vectors may genetically insert opsin proteins into both dividing and non-dividing cells. Example vectors can genetically insert opsin proteins in-vivo or in-vitro.

Those vectors that include a prokaryotic replicon may also include a prokaryotic promoter capable of directing the expression (transcription and translation) of the opsin protein in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment of the present invention. Examples of such vector plasmids are pUC8, pUC9, pBR322, and pBR329 available from BioRad Laboratories, (Richmond, Calif.) and pPL and pKK223 available from Pharmacia, (Piscataway, N.J.).

Expression vectors compatible with eukaryotic cells, may also be used. Eukaryotic cell expression vectors are well known in the art and are available from several commercial sources. Such vectors may be provided containing convenient restriction sites for insertion of the desired DNA homologue. Examples of such vectors are pKSV-10 (Pharmacia), pBPV-1/PML2d (International Biotechnologies, Inc.), and pTDT1 (ATCC, No. 31255).

One example of an expression vector is a lentivirus comprising the gene for ChR2 or Chop2 and an EF1-alpha promoter. This lentivirus vector may be used to create stable cell lines. The term "cell line" as used herein is an established cell culture that will continue to proliferate given the appropriate medium.

In one example, an expression vector is a lentivirus comprising the gene for the opsin and a cell specific promoter. Examples of cell specific promoters are promoters for somatostatin, parvalbumin, GABA$\alpha$6, L7, and calbindin. Other example cell specific promoters are promoters for kinases such as PKC, PKA, and CaMKII; promoters for other ligand receptors such as NMDAR1, NMDAR2B, G1uR2; promoters for ion channels including calcium channels, potassium channels, chloride channels, and sodium channels; and promoters for other markers that label classical mature and dividing cell types, such as calretinin, nestin, and beta3-tubulin.

Another example is a lentivirus containing tetracycline elements that allow control of the gene expression levels of ChR2 or NpHR, simply by altering levels of exogenous drugs such as doxycycline. This method, or other methods that place ChR2 or NpHR under the control of a drug-dependent promoter, will enable control of the dosage of ChR2 NpHR in cells, allowing a given amount of light to have different effects on electrical activation, substance release, or cellular development.

Nucleic acid sequences comprising the gene for opsin proteins and promoters for genetically targeted expression of the proteins may also be provided. The genetically targeted expression of the opsin proteins can be facilitated by the selection of promoters. The term "promoter" as used herein is nucleic acid sequence that enables a specific gene to be transcribed. The promoter may reside near a region of DNA to be transcribed. The promoter is usually recognized by an RNA polymerase, which, under the control of the promoter, creates RNA, which is then converted into the protein for which it codes. By use of the appropriate promoter, the level of expression of opsin protein can be controlled. Cells use promoters to control where, when, and how much of a specific protein is expressed. Therefore, by selecting a promoter that is selectively expressed predominantly within one type of cell, one subtype of cells, a given spatial region within an organism, or sub-cellular region within a cell, the expression of an opsin protein can be controlled accordingly. The use of promoters also allows the control of the amount of LACC expressed, and the timing of the expression. The promoters can be prokaryotic or eukaryotic promoters.

In one example, a nucleic acid sequence comprises the gene for an opsin protein and a general purpose promoter. A general purpose promoter allows expression of the opsin protein in a wide variety of cell types. One example of a general purpose promoter is the EF1-alpha promoter. The EF-1 alpha gene encodes for elongation factor-1 alpha which is one of the most abundant proteins in eukaryotic cells and is expressed in almost all kinds of mammalian cells. The promoter of this "housekeeping" gene can lead to persistent expression of the transgene in vivo. Another example promoter is the CMV (cytomegalovirus) promoter, which can drive gene expression at very high levels. Still other example general-purpose promoters include those for CaMKII and synapsin I (Dittgen et. al, PNAS 101:18206-11 (2004)).

In one example, a nucleic acid sequence comprising the gene for an opsin protein and a cell specific promoter is provided. Examples of cell specific promoters are promoters for somatostatin, parvalbumin, GABA$\alpha$6, L7, and calbindin. Other example cell specific promoters are promoters for kinases such as PKC, PKA, and CaMKII; promoters for other ligand receptors such as NMDAR1, NMDAR2B, G1uR2; promoters for ion channels including calcium channels, potassium channels, chloride channels, and sodium channels; and promoters for other markers that label classical mature and dividing cell types, such as calretinin, nestin, and beta3-tubulin. In one example, the nucleic acid comprises a bacterial artificial chromosome (BAC).

In one example, a promoter is an inducible promoter. For instance, the promoter may be inducible by a trans-acting factor which responds to an exogenously administered drug. The promoters may be, but are not limited to tetracycline-on or tetracycline-off, or tamoxifen-inducible Cre-ER.

In another example, a first opsin or set of opsins may be designed to activate a first population of cells upon exposure to a first wavelength of light or range of wavelengths, while a second opsin or set of opsins may be designed to inhibit a second population of cells upon exposure to the same wavelength or range of wavelengths of light, allowing for even more targeted control of the overall bioelectrical response of the target tissue or tissues.

Optical fibers 11 may be made from a plastic or glass, and as such may provide advantages over the leads and electrodes use for conventional electrical stimulation. First, because optical fibers 11 are not electrically conducting, they do not provide a galvanic path for induced currents at the tissue interface so there is no risk of tissue capture or excessive heating that can occur due to modalities such as magnetic resonance imaging (MRI) or electromagnetic interference (EMI). Moreover, the elimination of conductors from the tissue interface helps to mitigate MRI interference that is seen with typical electrical stimulation electrodes, allowing for continued high-resolution imaging post-implant. Second, because there is not a relatively large electrical current flowing through the target tissue, as is the case with electrical stimulation, optical stimulation does not mask or block the relatively smaller bioelectric activity that is electrically sensed at the same time optical stimulation is delivered. Thus, optical stimulation allows for simultaneous electrical sensing of the resulting reaction by the target tissue, allowing system 2 to provide for closed-loop feedback and control of the optical stimulation.

Figure 9:
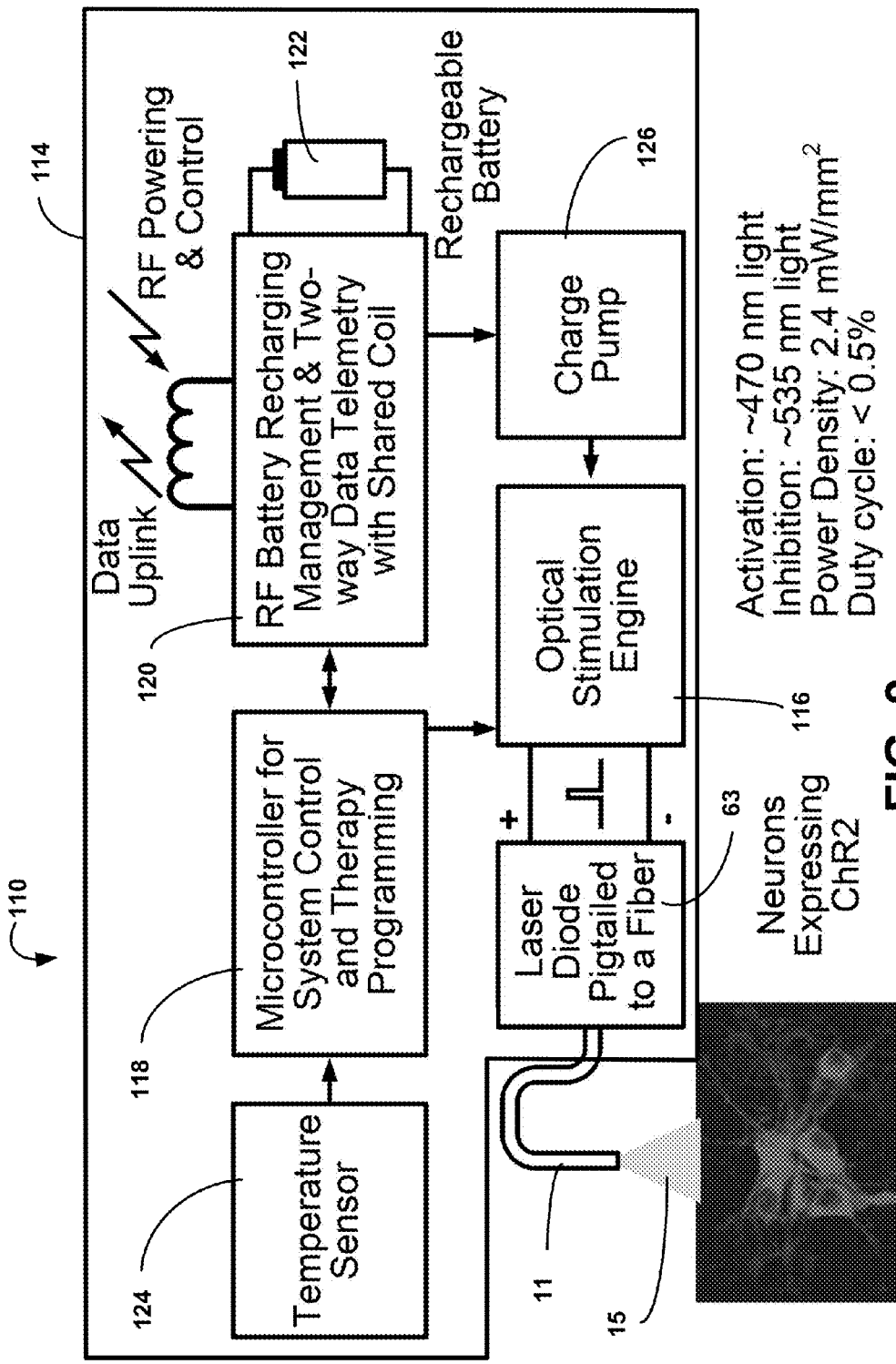
FIG. 9 is a block diagram of an example system for optogenetic neuromodulation of target neuron cells.

The architecture of an example implantable optogenetic neuromodulation system 110 is shown in FIG. 9. System 110 may comprise a hermetically-sealed chronic optical delivery system. System 110 may include an optical fiber 11 for light delivery, a fiber feedthrough 112, shown in FIG. 13, that couples optical fiber 11 to a light source 63 optically connected, or "pigtailed" to optical fiber 11, and provides a hermetic barrier between stimulator 114 and the tissue, an optical stimulation circuit 116 for driving light source 63, a microcontroller 118, also referred to as a processor, to manage system 110, a power source, such as a rechargeable battery 122, and an RF-power conditioning module 120 for bidirectional data communication and, if desired, recharging of the rechargeable battery 122. In one example, system 110 may include a temperature sensor 124 for use in implementing a closed-loop system to manage power flow in implant 114.

Examples of light source 63 that may be used in system 110 include one or more light-emitting diodes LEDs and one or more lasers. In one example, light source 63 may include one light source for activation of the target tissue, such as a light source to activate a channelrhodopsin-2 opsin, and another light source to inhibit the target tissue, such as a light source to activate a halorhodopsin opsin. Light source 63 may also include a light source to stop the activation of the target tissue, but not necessarily to inhibit the target tissue, such as a light source that deactivates or "switches off" the channelrhodopsin-2 opsin. In one example, light source 63 may comprise a standard commercially available LED tuned to a blue light wavelength of between about 459 nm and about 469 nm with an output power of between about 3.5 mW and about 5.5 mW for the activation of channelrhodopsin-2, a standard commercially available LED tuned to a green light wavelength of between about 515 nm and about 540 nm with an output power of between about 0.02 mW and about 1.5 mW for the deactivation of channelrhodopsin-2, and a standard commercially available LED tuned to a yellow light wavelength of about 558 nm with a power output of between about 0.02 mW and about 0.025 mW for activation of the halorhodopsin. In another example, light source 63 is one or more lasers that provide the optical stimulation to the target tissue. In one example, light source 63 may comprise a blue laser for the activation of channelrhodopsin-2, such as a standard commercially available semiconductor laser having a wavelength of about 470 nm with an output power of about 7.24 mW and a yellow laser for the activation of halorhodopsin, such as a standard commercially available semiconductor laser having a wavelength of about 532 nm with an output power of about 12 mW. If a battery power source is used, choice of the appropriate battery will depend on voltage, power and capacity/longevity needs that will depend on light source, circuitry and telemetry choices.

The system 110 may also include a charge pump 126 to convert the voltage of battery 122 to a voltage level appropriate to drive light source 63, and, in some examples, to convert the battery voltage to other voltage levels appropriate for other functions. The charge pump 126 may be tuned from 2× to 5× to accommodate power source voltage variation, such as battery voltage variation for a battery power source in the case of a primary battery or a rechargeable battery. In other words, charge pump 126 may be configured to provide different conversion ratios depending on the voltage level of the battery 122 over time as the battery discharges. Charge pump 126 may be a capacitive charge pump or an inductive charge pump, depending on the energy requirements of light source 63. For example, if light source 63 has a large power requirement, such as with a laser light source described in more detail below, than an inductive charge pump may be used because it is better at delivering higher power. Conversely, if light source 63 has low power requirements, such as with some low power light-emitting diodes (LEDs), then a capacitive charge pump may be used because it does not require the use of a bulky induction coil. In the example of FIG. 9, system 110 includes a rechargeable battery source 122 to power light source 63, which may be an LED-based light source, or possibly a higher voltage laser device. The battery source 122 may be recharged, e.g., by transcutaneous inductive transfer of energy from an external recharge device to a recharge circuit for the battery source.

Figure 10:
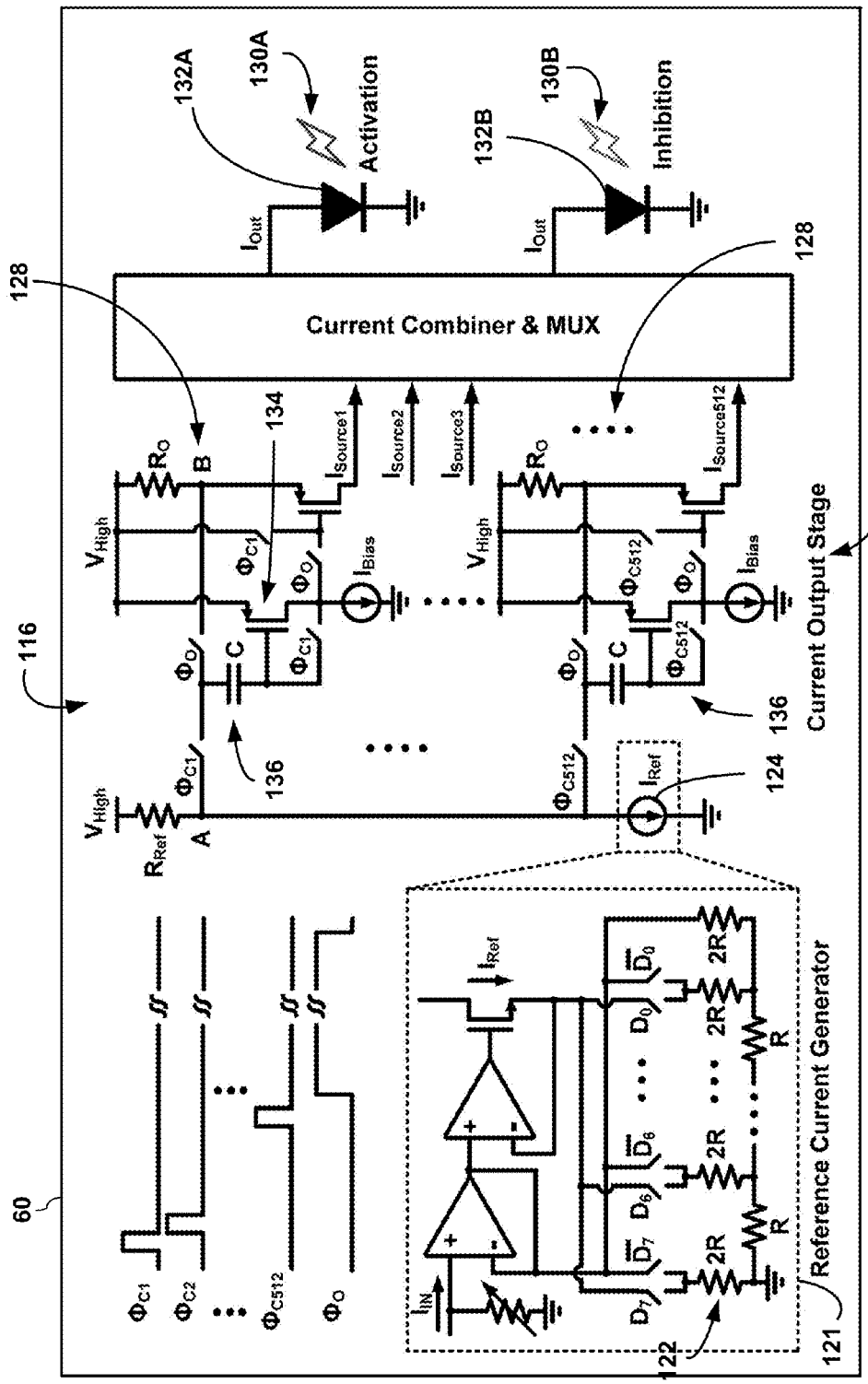
FIG. 10 is a schematic diagram of an example optical stimulation circuit.
Figure 11:
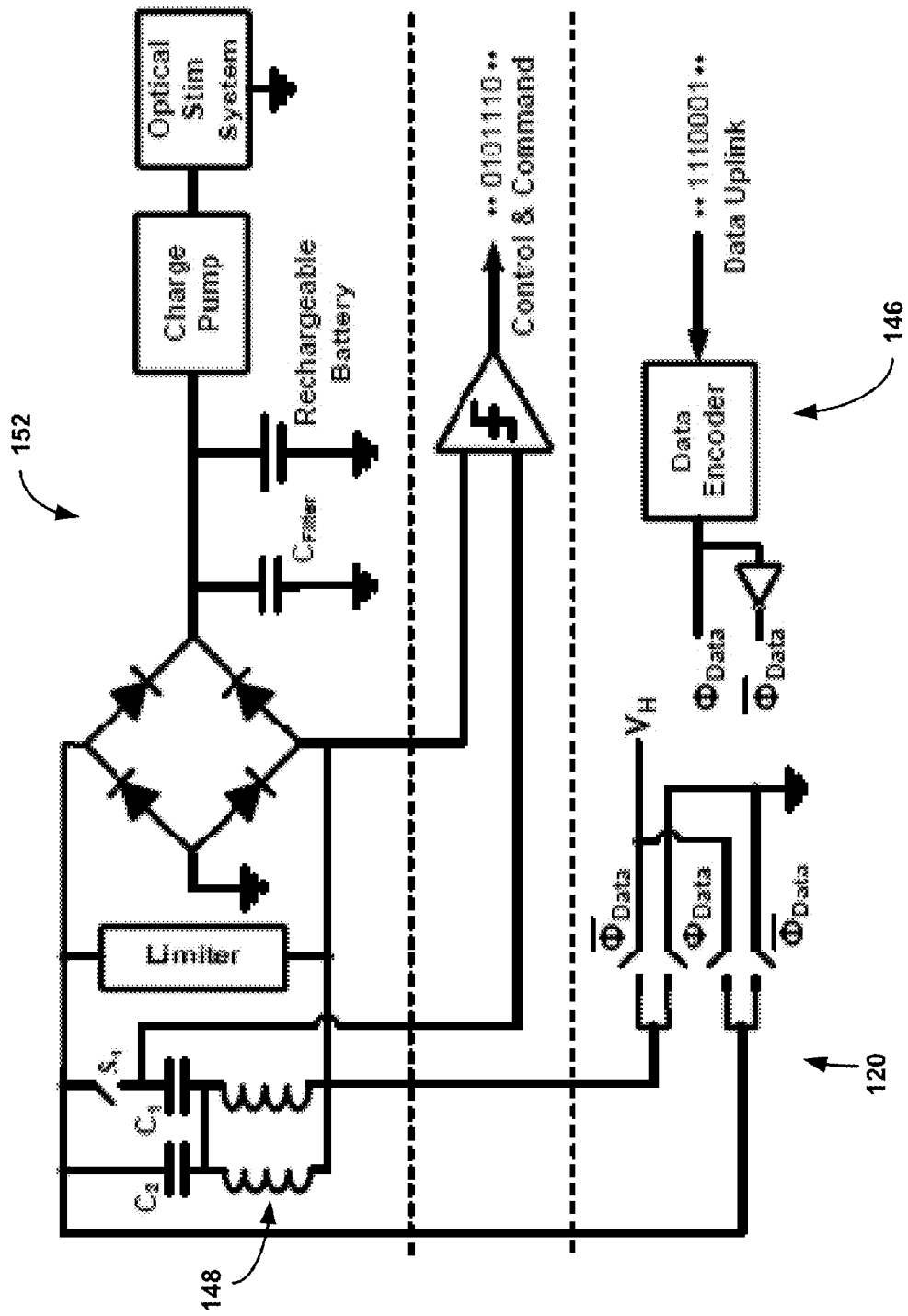
FIG. 11 is a schematic diagram of an example telemetry and power management circuit.

The circuit functionality of the system 110 may be partitioned into an optical stimulator circuit 116, shown in FIG. 10, a telemetry and power management circuit 120, shown in FIG. 11, and a microcontroller 118. In one example, optical stimulator circuit 116 and power management circuit 120 are fabricated as integrated circuits (ICs) in a 0.8 μm HV CMOS process.

Figure 13:
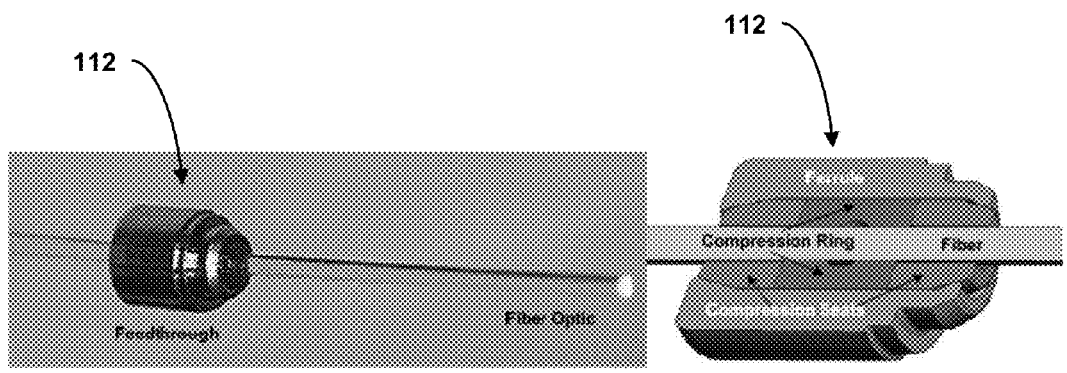
FIG. 13 is a photograph and cross-sectional view of an example compression feedthrough for passing an optical fiber through an optical stimulator housing.

Turning to FIG. 13, an example of a feedthrough 112 that may be used to provide a hermetic seal at the junction between optical fiber 11 and stimulator 4 is the optical feedthrough assembly disclosed in U.S. Pat. No. 7,349,618, entitled "Optical Feedthrough Assembly For Use In Implantable Medical Device," assigned to the assignee of this application, the entire disclosure of which is incorporated herein by reference.

Figure 14:
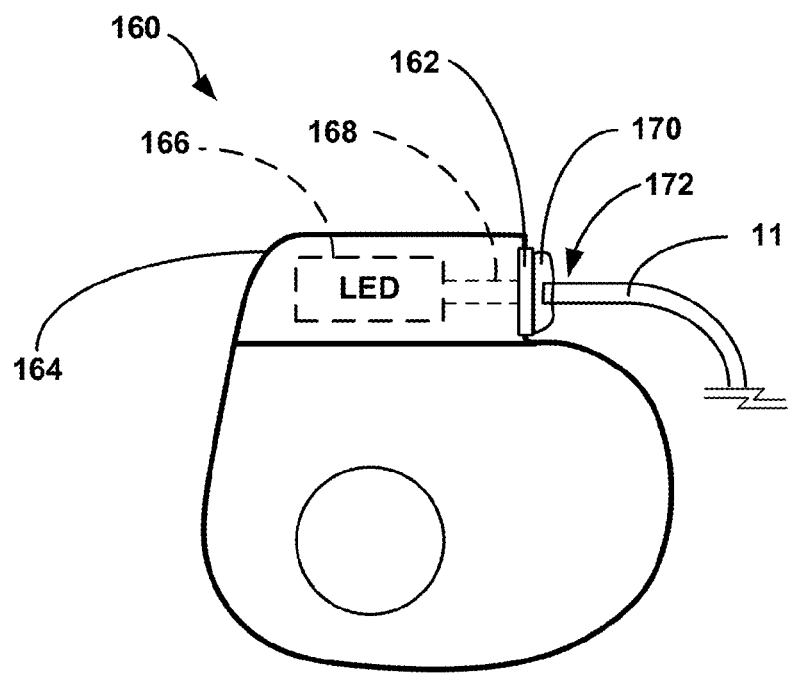
FIG. 14 is a conceptual diagram showing an example therapy system that includes an implantable optical stimulator coupled to an optical fiber through a window.

In another example, shown in FIG. 14, instead of a fiber feedthrough, an optical stimulation device 160 may comprise a window 162 formed in housing 164 of implantable stimulator 160, such as by hermetically sealing window 162 in stimulator housing 164. Hermetically-sealed window 162 may be optically connected to an optical light guide, such as optical fiber 11. Window 162 may also be optically connected to the output of a light source, such as an LED 166, within housing 164. The optical connection 168 between window 162 and LED 166 is shown schematically in FIG. 14. In one example, the optical connection between window 162 and optical fiber 11 is achieved through an optical index matching gel 170 applied to window 162. Index matching gel 170 ensures that the light produced by LED 166 maintains the desired wavelength, e.g. an excitation wavelength or inhibition wavelength corresponding to the light-sensitive channel protein at the target tissue, as described above. In this example, there is no need to have a feedthrough. Rather, the light from the light source 166 is delivered through window 162 to a proximal end 172 of the optically-connected optical fiber 11, such as through the index matching gel 170. This approach may provide more flexibility in terms of coupling the light source stimulation site because the window can be selected and configured to form part of the focusing optics for the light transmitted into the optical fiber. Examples of windows for use in transmitting light as described above are disclosed in U.S. Pat. No. 5,902,326 and PCT Publication No. WO2008/061135, both of which are assigned to the assignee of this application, the entire disclosures of which are incorporated herein by reference.

As discussed above with respect to FIG. 1, system 2 may also include one or more sense electrodes 17 carried on one or more implantable leads 12A, 12B to permit implantable stimulator 4 to sense electrical signals from patient 6. Implantable leads 12A, 12B may be carried on optical fiber bundle 10 and on each individual optical fiber 11. In this way, optical fiber bundle 10 and optical fibers 11 act as leads for carrying sense electrodes 17. In another example, one or more optical fibers 11 and one or more conducting leads 12 may be carried together as a unitary lead that contains both the one or more optical fibers 11 and the conducting lead 12. In one example, a unitary lead may contain both an optical fiber and a conducting lead, wherein sense electrodes are placed on a lead sheath that covers the optical fiber. In this example, the electrical conductors could be axial, running along the length of the lead with the optical fiber extending alongside the electrical conductor, or with the optical fiber being wound in a coil around the one or more electrical conductors, or with the electrical conductor being embedded within the optical fiber. In another example, the one or more electrical conductors may be wound in a coil, with the optical fiber extending inside the center of the coil, or with the optical fiber wound in a generally coaxial coil. In another example, rather than optical fibers, system 2 may include a lead that carries one or more electrical conductors that provide power to one or more light sources, such as an LED or a laser, located at the distal end of the lead. The lead may also carry one or more sense electrodes that are coupled to one or more of the electrical conductors carried by the lead. The conductors coupled to a light source or to a sense electrode may be arranged in any of the configurations described above with respect to electrical conductors or optical fibers above.

FIG. 1 further depicts a housing electrode 13 that may be used in conjunction with or in place of sense electrodes 17. In some cases, housing 14 may include multiple housing electrodes. Housing electrode 13 may be formed integrally with an outer surface of hermetically-sealed housing 14 of implantable stimulator 4, also referred to in this disclosure as implantable medical device (IMD) 4, or otherwise coupled to housing 14. Housing electrode 13 may be used to form unipolar electrode combinations with one or more electrodes carried on leads 12A, 12B to sense bioelectric potentials. Alternatively, electrodes carried on leads 12A, 12B may be used in bipolar or multipolar combinations to sense bioelectric potentials. To sense bioelectric potentials in proximity to the tissue illuminated by the optical stimulation, at least one of the electrodes in a given electrode combination should be positioned near the distal end of an optical fiber 11A, 11B.

A proximal end of fiber bundle 10 may be both optically and mechanically coupled to header 8 on implantable stimulator 4 either directly or indirectly via an optical extension. Alternatively, fiber bundle 10 may be optically and mechanically coupled to a window as described above. Optical fibers 11 permit passage of light energy along the body of optical fibers 11 to connect the distal ends of fibers 11 to a light source in implantable stimulator 4. Fiber bundle 10 traverses from the implant site of implantable stimulator 4 along the neck of patient 6 to cranium 18 of patient 6 to access brain 16. Optical fibers 11A and 11B may be implanted within the right and left hemispheres, respectively, in order to deliver optical stimulation to one or more regions of brain 16, which may be selected based on the patient condition or disorder. Alternatively, a single optical fiber 11 may be implanted at a specific treatment point within brain 16, or multiple optical fibers 11A, 11B may each be directed at the specific treatment target site, wherein the treatment target site may be selected based on the patient condition or disorder.

In the example of FIG. 1, implantable stimulator 4 may deliver, for example, deep brain stimulation (DBS) or cortical stimulation (CS) therapy to patient 6 via the optical fibers 11 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of fiber bundle 10 or optical fibers 11 shown in FIG. 1, or to the delivery of DBS or CS therapy.

Optical fibers 11 and lead segments 12A, 12B, if used, may be implanted within a desired location of brain 16 through respective holes in cranium 18. Optical fibers 11 may be placed at any location within brain 16 such that the emitted light 15 is capable of providing optical stimulation to targeted tissue during treatment. Example locations for optical fibers 11 within brain 16 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, optical fibers 11 may be implanted to provide stimulation to the visual cortex of brain 16 in order to reduce or eliminate migraine headaches afflicting patient 6. However, the target therapy delivery site may depend upon the patient condition or disorder being treated.

The sense electrodes 17 of lead segments 12A, 12B are shown as ring electrodes. Ring electrodes are commonly used in DBS applications because they are simple to program and are capable of sensing an electrical field to any tissue proximate to lead segments 12A, 12B. In other implementations, sense electrodes 17 of lead segments 12A, 12B may have different configurations. For example, the electrodes of lead segments 12A, 12B may have a complex electrode array geometry that is capable of sensing bioelectric potentials in a directional or localized manner.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust optical stimulation therapy. In particular, patient programmer 22 may permit patient 6 to adjust stimulation parameters of a program such as duration of treatment, optical intensity or amplitude, pulse width, pulse frequency, burst length, and burst rate. Patient 6 may also select a program, e.g., from among a plurality of stored programs, as the present program to control delivery of stimulation by implantable stimulator 4.

In some examples, implantable stimulator 4 delivers stimulation according to a group of programs at a given time. Each program of such a program group may include respective values for each of a plurality of therapy parameters, such as respective values for each of optical intensity or amplitude, pulse width, pulse shape, pulse rate, burst frequency, burst rate, burst width, and optical fiber configuration (e.g., the combination of optical fibers used and with what light intensity and wavelengths). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Figure 2:
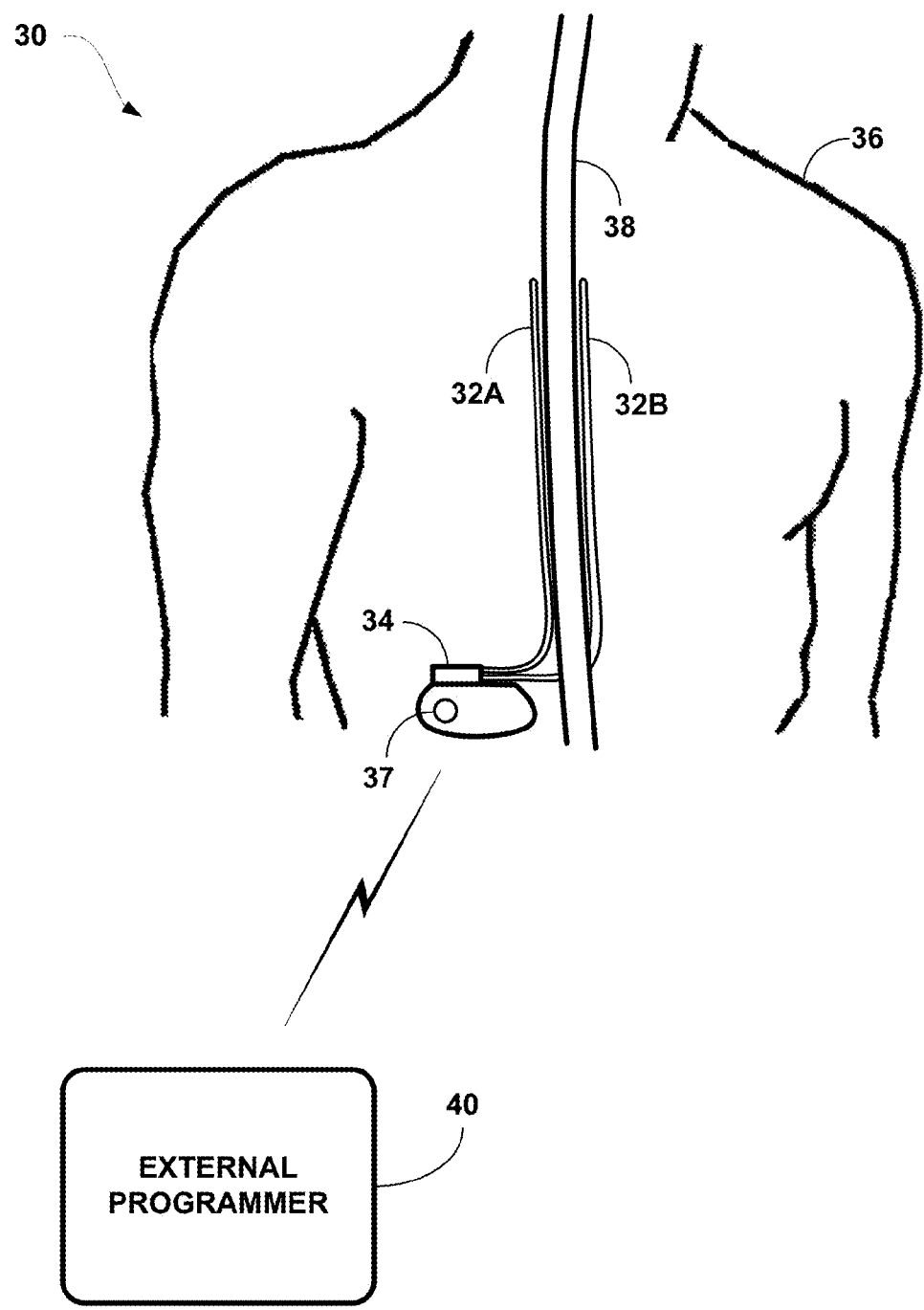
FIG. 2 is a conceptual diagram illustrating another example therapy system that includes an implantable stimulator coupled to one or more optical fibers.

FIG. 2 is a conceptual diagram illustrating system 30 that delivers stimulation therapy to spinal cord 38 of patient 36, also known as spinal cord stimulation (SCS). Other stimulation systems may be configured to deliver electrical stimulation to gastrointestinal organs, pelvic nerves or muscle, peripheral nerves, or other stimulation sites. In the example of FIG. 2, system 30 delivers optical stimulation therapy from implantable stimulator 34 to spinal cord 38 via one or more optical fibers 32A and 32B (collectively "optical fibers 32"). System 30 and, more particularly, implantable stimulator 34 may operate in a manner similar to implantable stimulator 4 (FIG. 1). That is, in one example, implantable stimulator 34 delivers controlled optical stimulation pulses or waveforms to patient 36 via one or more regulated stimulation optical fibers 32.

In the example of FIG. 2, the distal ends of optical fibers 32 are placed adjacent to the target tissue of spinal cord 38 such that light is emitted from the distal ends into the target tissue. The proximal ends of optical fibers 32 may be both optically and mechanically coupled to implantable stimulator 34 either directly or indirectly via a fiber extension and header. Alternatively, in some examples, optical fibers 32 may be implanted and coupled to an external stimulator, e.g., through a percutaneous port.

Stimulator 34 may be implanted in patient 36 at a location minimally noticeable to the patient. For SCS, stimulator 34 may be located in the lower abdomen, lower back, buttock or other location to secure the stimulator. Optical fibers 32 are tunneled from stimulator 34 through tissue to reach the target tissue adjacent to spinal cord 38 for optical stimulation delivery. Light is directed through optical fibers 32 so that the light is emitted from the distal ends of leads 32 in order to provide optical stimulation pulses from each optical fiber 32 to the target tissue. The stimulation pulses may be delivered using various optical fiber arrangements such as the use of a single optical fiber 32 to stimulate the target tissue or multiple optical fibers 32 arranged in a particular pattern around the target tissue. In one example, optical fibers 32 run along the spinal cord and shine light generally perpendicular to the axis of the spinal column. In one example, optical fibers 32 are anchored within or along the spinal column, such as with stereotactic techniques, to precisely position optical fibers 32 to provide the desired directionality of light emitted from optical fibers 32 and to prevent migration of optical fibers 32 after implantation. Anchoring of optical fibers 32 may prevent migration of optical fibers 32 during use and may also allow optical fibers 32 to be subjected to controlled bends to prevent light leakage from the optical fibers 32. In another example, optical fibers 32 allow for sharp angles within the small dimensions of the target tissue, such as in brain 16 or spinal cord 38. In another example, optical fibers are not used, but rather the light source is implanted at the target tissue at the end of an electrode, such as implanting a wire that extends from the stimulator 34 to the target tissue to power an LED to expose the target tissue to light. In another example, an LED is carried on the housing of a device that is implanted proximate the target tissue to expose the target tissue to light, while the device, such as a microstimulator device, may be connected to an implantable stimulator that is connected to the device by a wire. In still another example, an LED within the device housing may deliver light through a window in the device to target tissue proximate the window.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation delivered by implantable stimulator 34 may take the form of optical stimulation pulses or bursts, and may be characterized by controlled light intensity, as well as programmed pulse widths and pulse rates in the case of stimulation current pulses or controlled burst widths, burst frequencies, and burst rates for optical stimulation bursts. Stimulation may be delivered via selected combinations of optical fibers emitting light at multiple locations along the target tissue or at multiple target tissues. Stimulation of spinal cord 38 may, for example, prevent pain signals from traveling through the spinal cord and to the brain of the patient. Patient 36 perceives the interruption of pain signals as a reduction in pain and, therefore, efficacious therapy.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. In accordance with this disclosure, programmer 40 may transmit to the stimulator 34 information regarding the patient and regarding therapy the patient received during previous sessions including, for example, images that show placement of optical fibers 32.

In some cases, external programmer 40 may be characterized as a physician or clinician programmer, such as clinician programmer 20 (FIG. 1), if it is primarily intended for use by a physician or clinician. In other cases, external programmer 40 may be characterized as a patient programmer, such as patient programmer 22 (FIG. 1), if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate to implantable stimulator 34 or any other computing device via wireless communication. Programmer 40, for example, may communicate via wireless communication with implantable stimulator 34 using radio frequency (RF) telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 34 and other programming devices via remote telemetry techniques known in the art, communicating via a local area network (LAN), wide area network (WAN), public switched telephone network (PSTN), or cellular telephone network, for example.

Programming of stimulator 34 may also include graphically defining a desired stimulation field(s) within zones in one or more target tissues adjacent to the distal ends of one or more optical fibers 32, and generating, via a programmer, the optical stimulation required to create the stimulation field. Programming of stimulator 34 may also include translating one or more user input stimulation zones into a set of optical fibers 32 for delivering optical stimulation therapy to a patient, and a set of parameters such as pulse amplitudes, pulse widths, and pulse frequency associated with such optical fibers 32. Programming may further include manipulating the shape and position of the zone, including behaviors of the zone while moving and when colliding with other zones or system interlocks. As the stimulation zone is sized, moved, or shaped, the programmer may automatically compute updated optical fiber selections and parameters for delivery of stimulation indicated by the stimulation zone.

Figure 3:
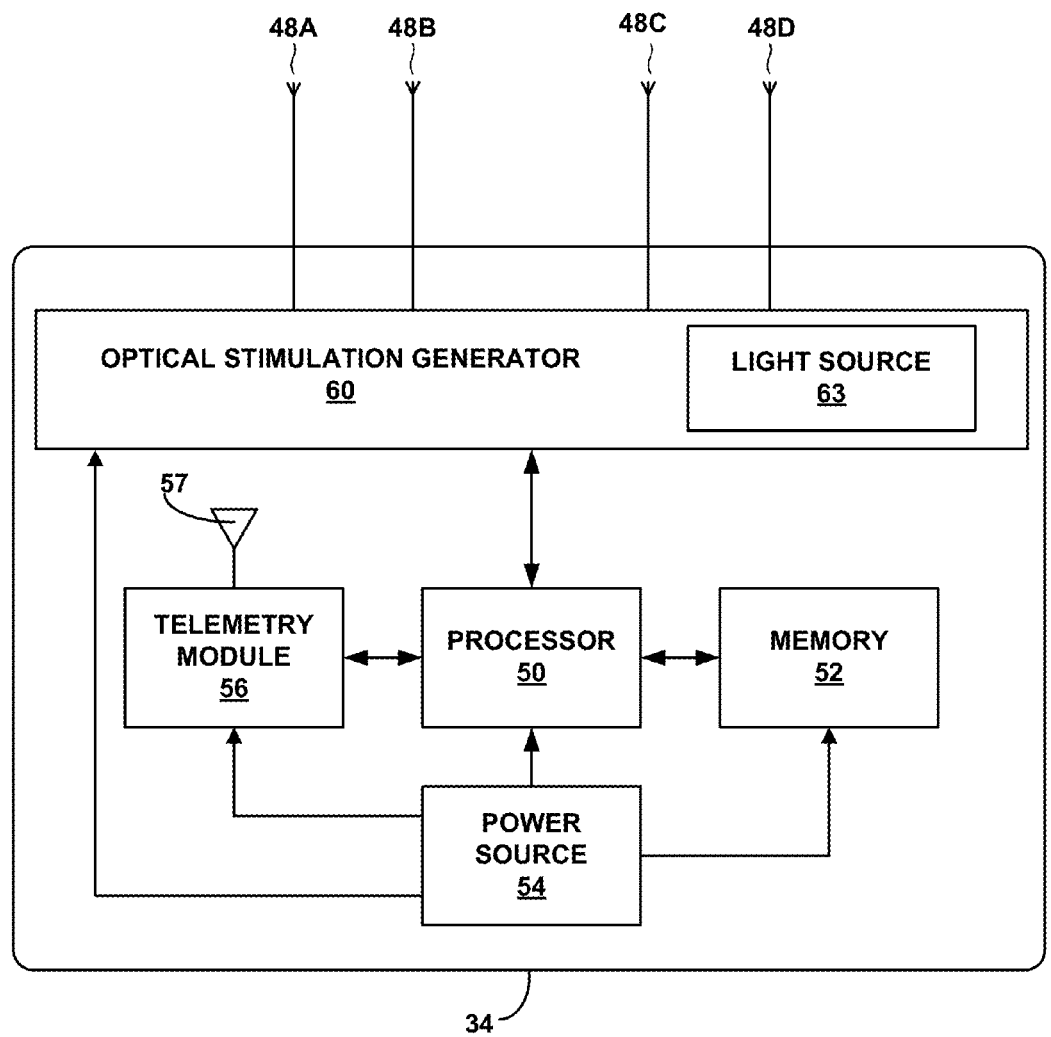
FIG. 3 is a block diagram illustrating various example components of an implantable optical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, telemetry module 56, antenna 57, and an optical stimulation generator 60 including a light source 63. Implantable stimulator 34 is also shown in FIG. 3 coupled to one or more implantable optical fibers 48A-D (collectively "optical fibers 48"). Implantable stimulator 34 may be a multi-channel device in the sense that it may be configured to include multiple optical paths (e.g., multiple light sources and optical fibers) that may deliver different optical stimulation waveforms, some of which may have different wavelengths. Although four optical fibers are shown in FIG. 3, more or less optical fibers may be used in different implementations, such as one, two, five or more optical fibers and associated light sources may be provided. The optical fibers may be detachable from a housing associated with implantable stimulator 34, or be fixed to such a housing.

In other examples, different optical fiber configurations of three optical fibers, four optical fibers, or more per target tissue may be provided. In addition, multiple optical fibers may be provided to a single target tissue site in the form of one or more optical fiber bundles that may be the same or different from fiber bundle to fiber bundle. In another example, a set of one or more optical fibers or fiber bundles may be provided to a first target tissue site while a second set of one or more optical fibers or fiber bundles may be provided to a second target tissue site. For example, a set of one or more optical fibers or fiber bundles may be directed to the subthalmic nucleus while another set of one or more optical fibers or fiber bundles may be directed to the pedunculopontine nucleus such that the combined use of the two sets of optical fibers may provide closed-loop deep brain stimulation to treat movement disorders such as Parkinson's disease, spasticity, epilepsy, and dystonia. In some cases, bioelectric signals may be sensed by the implanted device to detect onset of seizure, movement disorder symptoms, or other conditions, and trigger stimulation to alleviate such symptoms. As an additional example, the optogenetic stimulation may be applied to support a cell-targeted treatment for schizophrenia. In another example, two or more sets of optical fibers or optical fiber bundles may be placed at various epileptic foci and used for distributed treatment of the epileptic foci. In some examples, one or more optical fibers or fiber bundles may be selectively turned on or off in order to manage power.

Memory 52 may store instructions for execution by processor 50, optical stimulation therapy data, sensor data, and/or other information regarding therapy for patient 6. Processor 50 may control optical stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

In accordance with the techniques described in this disclosure, information stored on the memory 52 may include information regarding therapy that the patient 6 had previously received. Storing such information may be useful for subsequent treatments such that, for example, a clinician may retrieve the stored information to determine the therapy applied to the patient during his/her last visit, in accordance with this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver optical signals, e.g., as stimulation pulses, with intensities, wavelengths, pulse widths (if applicable), and rates specified by one or more stimulation programs. Processor 50 may also control optical stimulation generator 60 to selectively deliver the stimulation via subsets of optical fibers 48, also referred to as optical fiber combinations, and with stimulation specified by one or more programs. Different optical fibers may be directed to different target tissue sites.

Upon selection of a particular program group, processor 50 may control optical stimulation generator 60 to deliver optical stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. In addition, each program may specify a particular optical fiber combination for delivery of optical stimulation. The optical fiber combination may specify particular optical fibers in a single array or multiple arrays.

Optical stimulation generator 60 is optically coupled to optical fibers 48A-48D. Optical stimulation generator 60 may include stimulation generation circuitry to generate stimulation pulses and circuitry for switching stimulation across different optical fiber combinations, e.g., in response to control by processor 50. Optical stimulation generator 60 produces an optical stimulation signal in accordance with a program based on control signals from processor 50. Optical stimulation generator 60 may also include one or more light sources 63, such as one or more lasers or one or more light-emitting diodes (LEDs) that produce optical light within stimulator 34 that is then transmitted along optical fibers 48 to provide optical stimulation treatment to a target tissue. Alternatively, light source 63 may be separate from optical stimulation generator 60 such that optical stimulation generator 60 provides the signal that powers light source 63.

As described above, stimulator 34 delivers optical stimulation to the target neurons to activate one or more opsins that have been expressed in the target neurons. In one example, as described above, a first opsin is activated by a first wavelength of light so that the target neurons become permeable to cations to initiate neuronal spikes and fire the target neuron and a second opsin is activated by a second wavelength of light to deactivate or inhibit the target neurons. In this example, stimulator 34 may provide for a useful chronic device enabling continuous therapy by providing light at both the first wavelength and the second wavelength on an alternating or selective basis in order to provide for both selective activation and inhibition of the target neurons. For example, if chanelrhodopsin-2 is used as the activation opsin and halorhodopsin is used as the inhibition opsin, then optical stimulation generator 60, and particularly light source 63, may be configured to provide a first wavelength of between about 420 nm and about 475 nm, such as about 450 nm, to activate the channelrhodopsin-2 and activate the target neurons and a second wavelength of between about 510 nm and about 580 nm, such as about 535 nm, to activate the halorhodopsin and inhibit the target neurons. In another example, optical stimulation generator 60 may be configured to mimic more classical stimulation paradigms, such as by activating the standard, wild-type, channelrhodopsin-2 channel that acts as a light-activated transconductor, wherein the standard channelrhodopsin-2 channel may be activated by brief pulses of light with a wavelength of about 450 nm with an intensity of between about 8 mW/mm$^2$ and about 12 mW/mm$^2$ and a duty cycle of about 1% and a pulse frequency of between about 100 Hz and about 120Hz, such as a 100 µs pulse every 10 ms. In addition, because light scatters in tissue and the required voxel size for therapy may not be well established, optical stimulation generator 60 may be designed to be scaleable with the ability to incorporate multiple stimulation circuits and outputs to increase the volume of activation by using multiple pathways. In another example, one or more lenses may be used to focus or dissipate the light, as desired to provide more intense or scattered optical stimulation in the target tissue. In one example, a lens may be created at a distal end of an optical fiber by modifying or distorting the distal end to form a lens that may focus or dissipate light once it reaches the distal end.

Optical stimulation generator 60 may provide for the two wavelengths of stimulation light by having two light sources, one for each wavelength, such as a LED dedicated to each wavelength of light that feed into optical fibers 48 to deliver each wavelength of light to the target neurons depending on which LED is activated by optical stimulation generator 60 as controlled by processor 50. Alternatively, a single light source 63 that is capable of emitting both wavelengths may be used, such as a tunable LED or other tunable light source, wherein a particular wavelength is selected based on a treatment program run by processor 50 that causes optical stimulation generator 60 to control light source 63 to emit the selected wavelength, such as by tuning the tunable LED or other tunable light source to the selected wavelength.

Optical stimulation generator 60 may also control, under the direction of processor 50, several other parameters with respect to the optical stimulation of the target tissue, such as the intensity of light emitted to stimulate the target tissue, the number of pulses of light to be emitted, the pulse width, the frequency of pulses, and the pattern of pulses, including burst patterns wherein optical stimulation generator 60 may control burst width, burst frequency, the number of pulses per burst, and the number of bursts. In one example, optical stimulation generator 60 is capable of delivering light with an intensity of between about 1 mW/mm$^2$ and about 5 mW/mm$^2$. When light pulses are used as part of a stimulation program, optical stimulation generator 60 may, for example, produce pulses with a pulse width of between about 100 μs and about 15 ms, such as pulses with a pulse width of about 10 ms, and with a pulse frequency of between about 0.1 Hz and about 1 kHz, such as a frequency of about 0.2 Hz. In one example, optical stimulation generator 60 may drive optical stimulation with programmable modulation patterns that mimic existing patterns used in electrical stimulation for deep brain stimulation (DBS), and also allow for novel patterns that leverage the capabilities of the inhibitory optical transducer in the cell membranes.

In one example, shown in FIG. 10, optical stimulation generator 60 includes a stimulation engine circuit 116. In one example, optical stimulation engine 116 may include the capability to titrate pulse frequency and pulse width controlled via an external telemetry command and may provide programmable optical pulse trains to excite the transduction molecules. In one example, a constant current of 100 nA may be used to drive a reference current generator 121, which may consist of an R-2R-based digital-to-analog converter (DAC) 122 to generate an 8-bit reference current 124 with a maximum value of 5 μA. In this example, the reference current 124 is then amplified in a current output stage 126 with a gain set by the ratio of $R_O$ and $R_{Ref}$, which may be between 10 and 100, such as 40. With 512 current output stages 128, the optical stimulation circuit 116 can drive two optical outputs 130A, 130B for activation and inhibition with separate sources, each delivering a maximum current of 51.2 mA with 10 bit accuracy. In the example shown in FIG. 10, optical outputs 130A and 130B are shown as LEDs 132A and 132B, one for the activation wavelength and one for the inhibition wavelength of the opsins of the target neurons. The power requirements for optical components such as a LED or laser light source are generally larger than is required for conventional electrical stimulation. Moreover, the power required for optical components may be larger than that which can typically be provided by an implantable power source, such as a battery. Therefore, in one example, optical stimulation generator 60 includes a power management system within stimulation engine circuit 116 to allow power source 54 to provide power conditioning to boost the power provided by power source 54 to a level sufficient to power optical stimulation. Power management may be provided by the use of low overhead drivers to keep power dissipation low, and by an ability to modulate light intensity and its patterns as needed. In one example, a sense-resistor-based architecture may be used for current output stage 128 to eliminate the need to keep any output transistors 134 in saturation, reducing voltage headroom requirements to improve efficiency. A switched-capacitor 136 feedback may be used in current output stage 128 for low power consumption. The example optical stimulation circuit 116 shown in FIG. 10 may allow the stimulation pulse rate to be tuned from about 0.15 Hz to about 1 kHz and may allow tuning of the pulse width from about 100 μs to about 12 ms. Thus, optical stimulation generator 60 may be configurable, e.g., based on signals from processor 50, to store a desired voltage for delivery of optical stimulation light at an intensity specified by a program, and optical stimulation generator 60 may be configurable to deliver stimulation pulses with controlled pulse widths and pulse frequencies based on signals from processor 50.

Referring again to FIG. 3, telemetry module 56 may include a radio frequency (RF) transceiver to permit bi-directional communication between implantable stimulator 34 and each of clinician programmer 20 and patient programmer 22. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 34 or take the form of a circuit trace on the circuit board. In this way, telemetry module 56 may permit communication with clinician programmer 20 and patient programmer 22 in FIG. 1 or external programmer 40 in FIG. 2, to receive, for example, new programs or program groups, or adjustments to programs or program groups. Telemetry module 56 may also permit communication with clinician programmer 20 to receive, for example, an image captured by the programmer of the lead placement along with information regarding the captured image and the therapy received by the patient during previous sessions, in accordance with this disclosure. Telemetry module 56 may also communicate information regarding previous therapy sessions that have been stored in memory 52, to an external programmer during a subsequent therapy session; the information regarding a previous therapy session may have been imported by a programmer used in the previous session.

Power source 54 may be a non-rechargeable primary cell battery or a rechargeable battery and may be coupled to power circuitry. However, the disclosure is not limited to examples in which the power source is a battery. In another example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4. In some examples, power requirements may be small enough to allow stimulator 4 to utilize patient motion at least in part and implement a kinetic energy-scavenging device to trickle charge a rechargeable battery. A voltage regulator may generate one or more regulated voltages using the battery power.

In one example, telemetry and power management may be controlled through a circuit 120, shown schematically in FIG. 11. Telemetry and power management circuit 120 provides for a bidirectional telemetry and RF-charging system. In one example, the telemetry carrier frequency is 175 kHz to align with a common ISM band and uses OOK at 4.4 kbps to stay within regulatory limits. A telemetry decoder 142 may use a chopper amplifier circuit, such as the chopper amplifier circuit described in Denison et al., "A 2 µW 100 nV/rtHz Chopper-Stabilized Instrumentation Amplifier for Chronic Measurement of Neural Field Potentials," IEEE Journal of Solid-State Circuits, vol. 43, pp. 2934-45 (2007), or as described in commonly assigned U.S. Patent Application Publication No. 2008/0269841, to Grevious et al., entitled "Chopper Mixer Telemetry Circuit," or as described in commonly assigned U.S. Patent Application Publication No. 2008/01800278, to Denison, entitled "Chopper-stabilized Instrumentation Amplifier for Wireless Telemetry," the entire disclosure of each of which is incorporated herein by reference, which may be configured as a combined down mixer-amplifier. An uplink 146 may be an H-bridge driver. One or more telemetry capacitors 148 may provide a tuning range of 50-130 kHz.

The system may include a temperature sensor, such as temperature sensor 124 shown in FIG. 9, to monitor the temperature at stimulator 34 or proximate to stimulator 34 during optical stimulation and recharge. Temperature sensor 124 may be used to adjust light delivery to the target tissue based on the temperature sensed by temperature sensor 124. For example, temperature sensor 124 may be used to ensure that the peak temperature is constrained to under a 2° C. increase over nominal body temperature per FDA guidelines, which can be a concern for driving less efficient opsin channels. In one example, if temperature sensor 124 determines a rise in temperature above a permitted temperature, such as more than about a 2° C. increase over nominal body temperature, power management circuit 120 will modulate power in the device to avoid overheating of tissue and send an alert to processor 50. In another example, processor 50 may cease optical stimulation and, in some examples, switch to electrical stimulation to mitigate the risk of overheating. In another example, adjusting the delivery of light from light source 63 may comprise one or more of: adjusting a pulse rate, a pulse width, an amplitude intensity, or a duty cycle of light delivered from light source 63. Light source 63 is controlled by microcontroller 118, which may receive signals from temperature sensor 124, and optical stimulation engine 116. Thus, it will be understood that any of the embodiments that provide optical stimulation may also deliver electrical stimulation.

Figure 4:
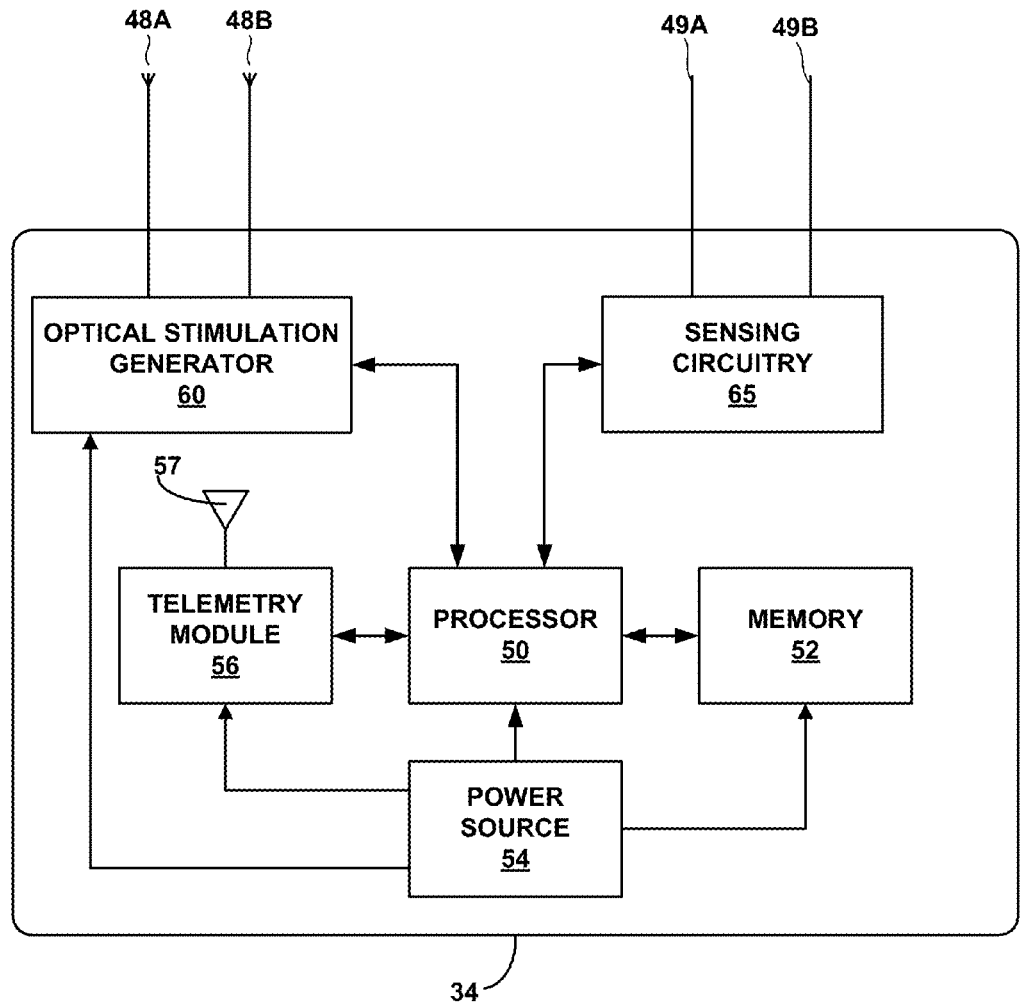
FIG. 4 is a block diagram illustrating the example components of another example implantable optical stimulator with a sensing generator.

FIG. 4 is a block diagram illustrating various components of another example implantable stimulator 34. Like the implantable stimulator 34 shown in FIG. 3, the example of FIG. 4 includes an optical stimulation generator 60, a processor 50, memory 52, a telemetry module 56, and a power source 54 which have the same general configurations as described above for the example of FIG. 3. The example stimulator 34 of FIG. 4 also includes sensing circuitry 65 electrically coupled to one or more leads 49A, 49B (collectively referred to as "leads 49") that each carry one or more sense electrodes, such as sense electrodes 17 shown in FIG. 1. Sensing circuitry 65 receives electrical signals from the sense electrodes along leads 49 to provide for sensing of bioelectric activity within the patient before, during, and after optical stimulation controlled by optical stimulation generator 60.

Figure 7:
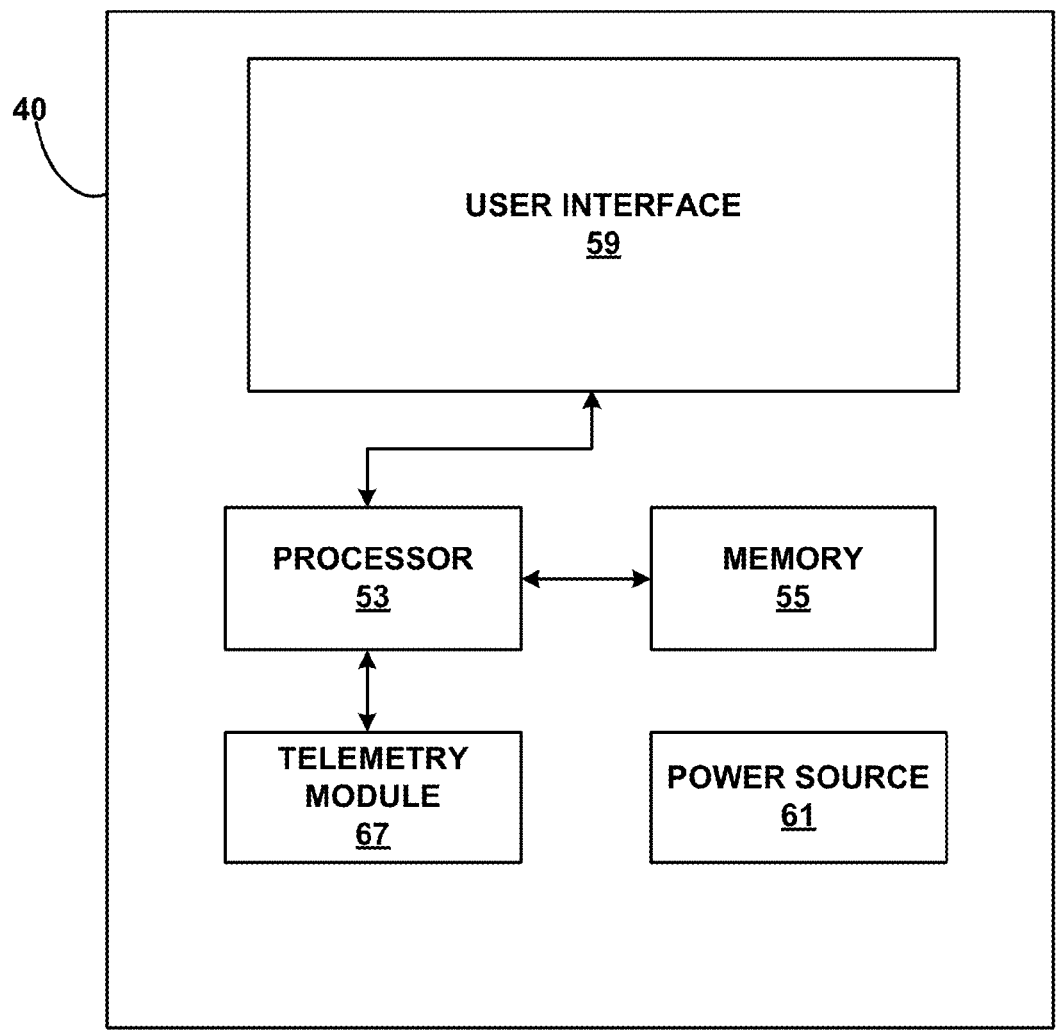
FIG. 7 is a block diagram illustrating various example components of an external programmer.

FIG. 7 is a functional block diagram illustrating various components of an external programmer 40 for an implantable stimulator 14. Although the components shown in FIG. 7 are described in reference to external programmer 40, the components may also be included within clinician programmer 20 or patient programmer 22 shown in FIG. 1. As shown in FIG. 7, external programmer 40 includes processor 53, memory 55, telemetry module 67, user interface 59, and power source 61. In general, processor 53 controls user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

A clinician or patient 36 interacts with user interface 59 in order to, for example, manually select, change or modify programs, adjust optical amplitude, pulse width, pulse rate, and other stimulation parameters, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 67 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 67 which may be coupled to an internal antenna or an external antenna. Telemetry module 67 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

In other examples, rather than being a handheld computing device or a dedicated computing device, programmer 40 may be a larger workstation or a separate application within another multi-function device. For example, the multi-function device may be a cellular phone, personal computer, laptop, workstation computer, or personal digital assistant that can be configured with an application to simulate programmer 40. Alternatively, a notebook computer, tablet computer, or other personal computer may enter an application to become programmer 40 with a wireless adapter connected to the personal computer for communicating with stimulator 34.

Figure 5:
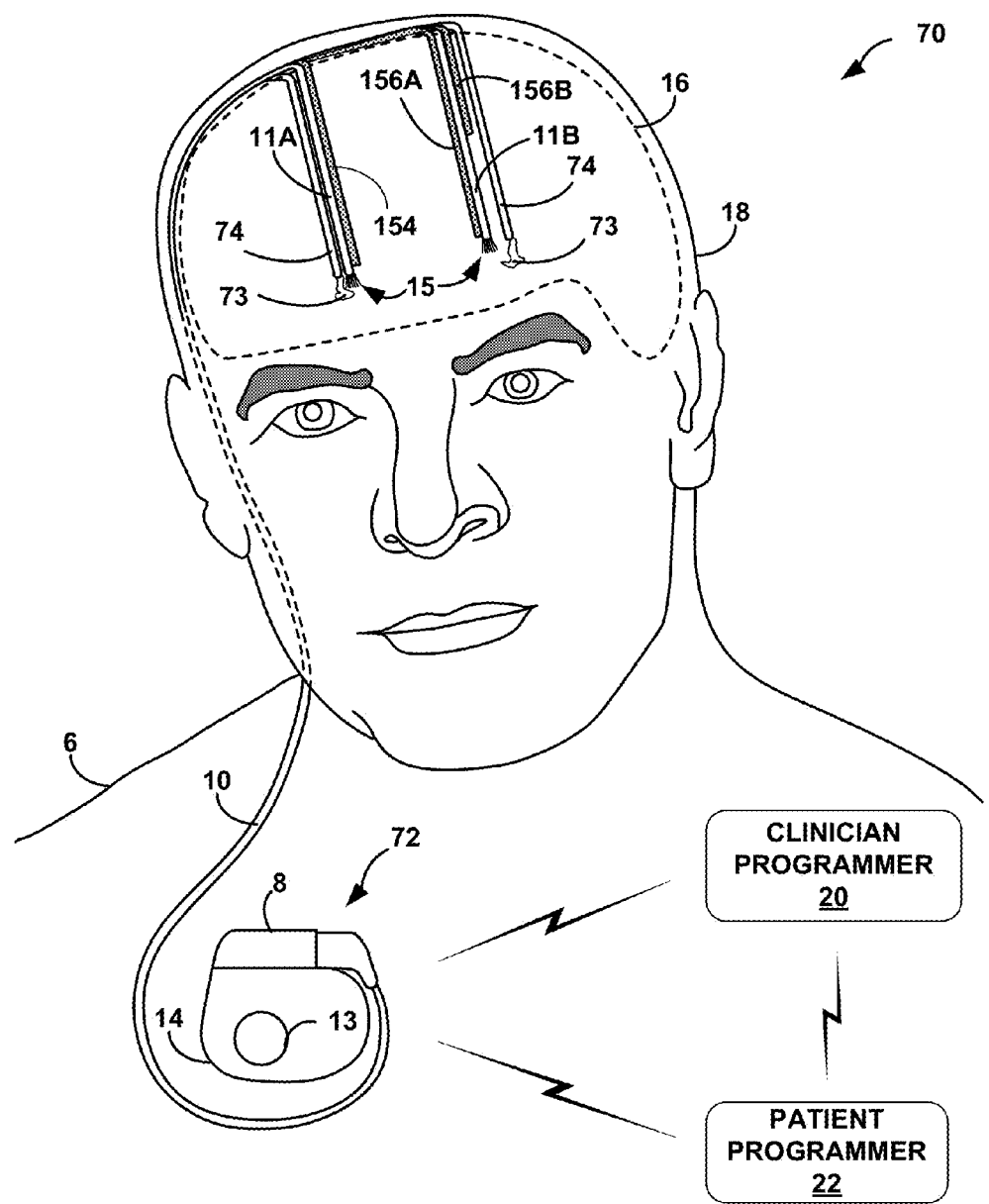
FIG. 5 is a conceptual diagram illustrating another example therapy system that includes an implantable stimulator coupled to one or more optical fibers for optical stimulation and one or more catheters for delivery of a therapeutic agent.

A conceptual diagram illustrating another example therapy system 70 is shown in FIG. 5. Like systems 2 and 30 described above, therapy system 70 is used to deliver optical stimulation therapy to patient 6. Therapy system 70 includes an implantable medical device (IMD) 72 that delivers optical stimulation to patient 6 via one or more implantable optical fibers 11. The optical stimulation provided by IMD 72 is essentially the same as described above for simulator 4 in FIG. 1 and stimulator 34 in FIG. 2. IMD 72 also may provide the ability to deliver a therapeutic agent 73 to a target site within patient 6. An example therapeutic agent that IMD 72 may be configured to deliver is a gene therapy agent that provides targeted delivery of a light-sensitive ion channel protein, also referred to as an "opsin," to specific target cells, such as neurons within brain 16 or the spinal cord of patient 6, such as by contacting the target cells with a vector, such as a lentivirus or a retrovirus, comprising a nucleic acid sequence that codes for the opsin so that the target cells express the opsin.

In the example of FIG. 5, the therapeutic agent is a therapeutic fluid, which IMD 72 delivers to patient 6 through one or more catheters 74 coupled to IMD 72 that are implanted so that a distal end of catheter 74 is located proximate to the target cells. Stereotactic techniques or other positioning techniques may be used to precisely position fluid delivery catheters and/or optical fibers with respect to target tissue sites and to maintain the precise positioning throughout use. In some examples, after positioning, one or more fluid delivery catheters and/or optical fibers may be held precisely in place using fixation techniques or mechanisms such as those similar to the Medtronic StimLoc™ burr hole cover, manufactured by Medtronic, Inc., of Minneapolis, Minn. In some examples, the optical stimulation generator, i.e., including a light source, controller, power source, and telemetry circuitry, could be formed as a microstimulator that is structurally mounted on or integrated with a burr hole cover, such as a StimLoc™ burr hole cover. In this case, the optical fiber would run only from the skull to deep brain structures, instead of running from an implant pocket, such as an implant pocket near the clavicle. For this example, in some cases, the microstimulator device can be anchored to the skull using one or more bone morphogenetic proteins (BMPs), which is a material used in spine and biologics procedures to fuse cervical or spinal discs.

In one example, one or more catheters 74 are provided to deliver the therapeutic agent 73 at or near the same location within the target tissue that is exposed to light 15 so that the therapeutic agent will promote expression of opsin by the target tissue at the same point where the target tissue will be exposed to optical stimulation. Catheters 74 could be side by side with optical fibers 11, as shown in FIG. 5, or the optical fibers and fluid delivery conduits may be combined into a common unitary lead, such as within separate lumens within the unitary lead with a fluid conduit in side-by-side arrangement with an optical fiber or in a coaxial arrangement with the optical fiber being within the fluid conduit or vice versa. In one example (not shown), the optical fiber that delivers light stimulation to the target tissue may be a fiber with a hollow core so that light is passed through the outer fiber portion while the therapeutic agent is passed through the hollow core. In this case, the fiber may have an annular cross-section. In yet another example, a conduit may be provided that delivers the therapeutic agent to the target tissue while the optical fiber is threaded through the conduit such that the therapeutic agent is delivered in the annular region between the outer diameter of the optical fiber and the inner wall of the lead body.

Catheter 74 can comprise a unitary catheter or a plurality of catheter segments connected together to form an overall catheter length. An external programmer, such as clinician programmer 20 or patient programmer 22 or the external programmer 40 shown in FIG. 7, is configured to wirelessly communicate with IMD 72 as needed, such as to provide or retrieve therapy information or control aspects of therapy delivery (e.g., modify the therapy parameters such as rate or timing of delivery, turn IMD 72 on or off, and so forth) from IMD 72 to patient 6.

IMD 72 may be implanted within a subcutaneous pocket relatively close to the therapy delivery site. For example, in the example shown in FIG. 5, IMD 72 is implanted within a clavicle region of patient 6 so that IMD 72 may deliver the therapeutic agent to brain 16 of patient 6. In other examples, IMD 72 may be implanted within other suitable sites within patient 6, which may depend, for example, on the target site within patient 6 for the delivery of the therapeutic agent, such as within the abdomen for delivery of the therapeutic agent to the spinal cord of patient. In still other examples, IMD 72 may be external to patient 6 with a percutaneous catheter connected between IMD 72 and the target delivery site within patient 6.

Catheter 74 may be coupled to IMD 72 either directly or with the aid of a catheter extension (not shown in FIG. 5). In the example shown in FIG. 5, catheter 74 traverses from the implant site of IMD 72 to one or more target sites. Catheter 74 is positioned such that one or more fluid delivery outlets (not shown in FIG. 5) of catheter 74 are proximate to the target sites within patient 6. In the example of FIG. 5, IMD 72 delivers a therapeutic agent through catheter 74 to target sites within brain 16. IMD 72 may be configured for intrathecal delivery into the intrathecal space, as well as epidural delivery into the epidural space, both of which surround the spinal cord. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord. The intrathecal space is within the subarachnoid space, which is further inward past the epidural space and dura mater and through the theca.

Although the target site shown in FIG. 5 is within brain 16 of patient 6, other applications of therapy system 70 include alternative target delivery sites. The target delivery site in other applications of therapy system 70 can be located within patient 6 proximate to, e.g., sacral nerves (e.g., the S2, S3, or S4 sacral nerves), the spinal cord, or any other suitable nerve, organ, muscle or muscle group in patient 6, which may be selected based on, for example, a patient condition. In one such application, therapy system 70 may be used to deliver a therapeutic agent to tissue proximate to a pudendal nerve, a perineal nerve or other areas of the nervous system, in which cases, catheter 74 would be implanted and substantially fixed proximate to the respective nerve. As another example delivery site, catheter 74 may be positioned to deliver a therapeutic agent to a deep brain site or within the heart (e.g., intraventricular delivery of the agent) or blood vessels. Delivery of a therapeutic agent within brain 16 may help manage any number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. In one example, the target site to which therapeutic agent is delivered via catheter 74 is proximate to the site that is stimulated by light 15 from optical fibers 11 so that the therapeutic agent 73 will modify the target cells that are desired to be stimulated by light 15. In one example, described in more detail below, the therapeutic agent is a gene therapy fluid that modifies neurons within brain 16 to form opsins that are sensitive to the wavelength of light that is emitted by optical fibers 11.

In one example, IMD 72 can deliver one or more therapeutic agents to patient 6 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 72 may be configured to deliver a therapeutic agent to patient 6 according to different therapy schedules on a selective basis. IMD 72 may include a memory to store one or more therapy programs, instructions defining the extent to which patient 6 may adjust therapy parameters, switch between dosing programs, or undertake other therapy adjustments. Patient 6 or a clinician may select and/or generate additional dosing programs for use by IMD 72 via an external programmer at any time during therapy or as designated by the clinician.

In some examples, a single catheter 74 or multiple catheters 74 may be coupled to IMD 72 to target the same or different tissue or nerve sites within patient 6. Thus, although two catheters 74 are shown in FIG. 5, in other examples, system 70 may include a single catheter, or more than two catheters, or the single or multiple catheters 74 may define multiple lumens for delivering different therapeutic agents to patient 6 or for delivering a therapeutic agent to different tissue sites within patient 6. Accordingly, in some examples, IMD 72 may include a plurality of reservoirs for storing more than one type of therapeutic agent. In some examples, IMD 72 may include a single long tube that contains the therapeutic agent in place of a reservoir. However, for ease of description, an IMD 72 including a single reservoir is primarily discussed in this disclosure with reference to the example of FIG. 5.

The external programmer that is used to program IMD 72, such as programmer 40 shown in FIG. 7, is an external computing device that is configured to communicate with IMD 72 by wireless telemetry. For example, the programmer may be a clinician programmer that the clinician uses to communicate with IMD 72 and program therapy delivered by IMD 72. Alternatively, the programmer may be a patient programmer that allows patient 6 to view and modify therapy parameters associated with therapy programs. In one example the external programmer to program IMD 72 is the same external programmer 40 that is used to program stimulator 2 shown in FIG. 1 or to program stimulator 34 shown in FIG. 2, 3, or 4. The clinician programmer may include additional or alternative programming features than the patient programmer. For example, more complex or sensitive tasks may only be allowed by the clinician programmer to prevent patient 6 from making undesired or unsafe changes to the operation of IMD 72. In one example, programmer 40 to control the delivery of the therapeutic agent through catheter 74 is included as part of clinician programmer 20 or patient programmer 22 described with respect to FIG. 1 so that the programmer 20, 22, 40 provides control over the delivery of optical stimulation therapy and the therapeutic agent.

When programmer 40 is configured for use by the clinician, programmer 40 may be used to transmit initial programming information to IMD 72. This initial information may include hardware information for system 70 such as the type of catheter 74, the position of catheter 74 within patient 6, the type and amount, e.g., by volume of therapeutic agent(s) delivered by IMD 72, frequency of introduction of therapeutic agent(s), a refill interval for the therapeutic agent(s), a baseline orientation of at least a portion of IMD 72 relative to a reference point, therapy parameters of therapy programs stored within IMD 72 or within programmer 40, and any other information the clinician desires to program into IMD 72.

The clinician uses programmer 40 to program IMD 72 with one or more therapy programs that define the therapy delivered by IMD 72. During a programming session, the clinician may determine one or more dosing programs that may provide effective therapy to patient 6, such as the frequency for the introduction of a gene therapy agent to a target tissue within patient 6. Patient 6 may provide feedback to the clinician as to efficacy of a program being evaluated or desired modifications to the program. Once the clinician has identified one or more programs that may be beneficial to patient 6, the patient may continue the evaluation process and determine which dosing program or therapy schedule best alleviates the condition of the patient or otherwise provides efficacious therapy to the patient.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental doses, a maximum dose that may be delivered over a given time interval, and so forth. IMD 72 may include a feature that prevents dosing the therapeutic agent in a manner inconsistent with the dosing program. Programmer 40 may assist the clinician in the creation/identification of dosing programs by providing a methodical system of identifying potentially beneficial therapy parameters. In one example, the dosing program may be coordinated with the optical stimulation provided by stimulator 34. For example, a dose of the therapeutic agent may be delivered, followed by a period of inactivity to allow the therapeutic agent to transfect the cells at the target site, such as for a few hours or a few days depending on the known time needed for the therapeutic agent to transfect the neurons, followed by an optical stimulation program, such as a program of light pulses having a particular pulse width, pulse frequency, and light wavelength and intensity. The optical stimulation may be followed up by a second dose of therapeutic agent. In another example, the dosing program may include one or more boluses of therapeutic agent delivered at selected times or intervals.

In some cases, programmer 40 may also be configured for use by patient 6. When configured as the patient programmer, programmer 40 may have limited functionality in order to prevent patient 6 from altering critical functions or applications that may be detrimental to patient 6. In this manner, programmer 40 may only allow patient 6 to adjust certain therapy parameters or set an available range for a particular therapy parameter. Programmer 40 may also provide an indication to patient 6 when therapy is being delivered or when IMD 72 needs to be refilled or when the power source within programmer 40 or IMD 72 need to be replaced or recharged.

Whether programmer 40 is configured for clinician or patient use, programmer 40 may communicate to IMD 72 or any other computing device via wireless communication. Programmer 40, for example, may communicate via wireless communication with IMD 72 using radio frequency (RF) telemetry techniques. Programmer 40 may also communicate with another programmer or computing device via a wired or wireless connection using any of a variety of communication techniques including, e.g., RF communication according to the 802.11 or Bluetooth specification sets, infrared (IR) communication according to the IRDA specification set, or other standard or proprietary telemetry protocols. Programmer 40 may also communicate with another programming or computing device via exchange of removable media, such as magnetic or optical disks, or memory cards or sticks including, e.g., non-volatile memory. Further, programmer 40 may communicate with IMD 72 and another programmer via, e.g., a local area network (LAN), wide area network (WAN), public switched telephone network (PSTN), or cellular telephone network, or any other terrestrial or satellite network appropriate for use with programmer 40 and IMD 72.

Figure 6:
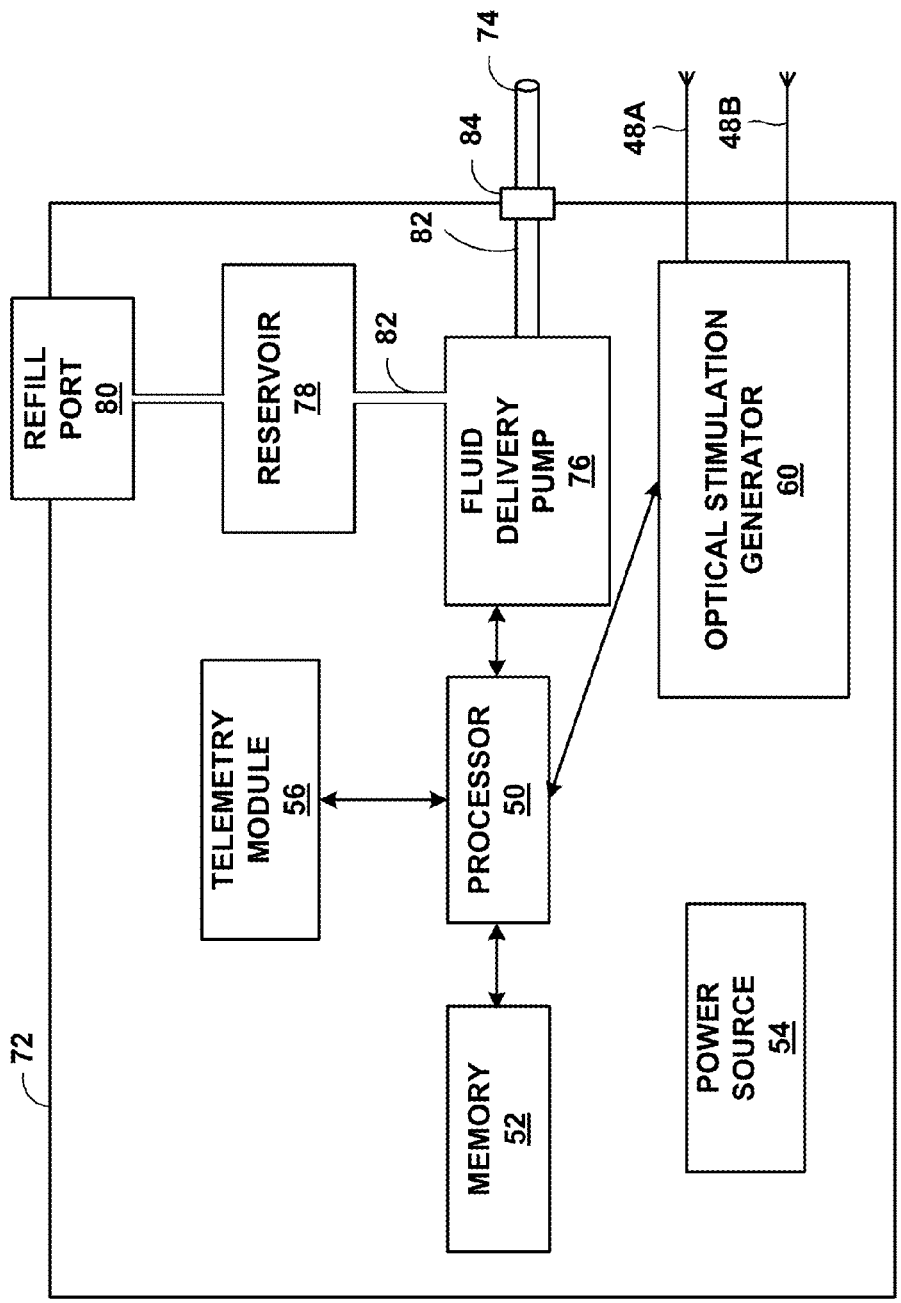
FIG. 6 is a block diagram illustrating various example components of the implantable stimulator and fluid delivery device of FIG. 5.

FIG. 6 is a functional block diagram illustrating components of an example of IMD 72, which includes a processor 50, memory 52, telemetry module 56, fluid delivery pump 76, reservoir 78, refill port 80, internal tubing 82, catheter access port 84, and power source 54. Processor 50, memory 52, telemetry module 56, and power source 54 may be the same components as those described above with respect to FIG. 3. Processor 50 is communicatively connected to memory 52, telemetry module 56, and fluid delivery pump 76. Fluid delivery pump 76 is in fluid communication with reservoir 78 and catheter access port 84 via internal tubing 82. Reservoir 78 is connected to refill port 80. Catheter access port 84 is connected to internal tubing 82 and catheter 74. IMD 72 also includes power source 54, which is configured to deliver operating power to various components of the IMD.

During operation of IMD 72, processor 50 controls fluid delivery pump 76 with the aid of instructions associated with program information that is stored in memory 52 to deliver a therapeutic agent to patient 6 via catheter 74. Instructions executed by processor 50 may, for example, define dosing programs and/or therapy schedules that specify the amount of a therapeutic agent that is delivered to a target tissue site within patient 6 from reservoir 78 via catheter 74. The instructions may further specify the time at which the therapeutic agent will be delivered and the time interval over which the agent will be delivered. The amount of the agent and the time over which the agent will be delivered are a function of, or alternatively determine, the dosage rate at which the fluid is delivered. The therapy programs may also include other therapy parameters, such as the frequency of dose delivery, the type of therapeutic agent delivered if IMD 72 is configured to deliver more than one type of therapeutic agent, and so forth. Components described as processors within IMD 72, external programmer 40, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Upon instruction from processor 50, fluid delivery pump 76 draws fluid from reservoir 78 and pumps the fluid through internal tubing 82 to catheter 74 through which the fluid is delivered to patient 6 to effect one or more of the treatments described above. Internal tubing 82 is a segment of tubing or a series of cavities within IMD 72 that run from reservoir 78, around or through fluid delivery pump 76 to catheter access port 84. Fluid delivery pump 76 can be any mechanism that delivers a therapeutic agent in some metered or other desired flow dosage to the therapy site within patient 6 from reservoir 78 via implanted catheter 74.

In one example, fluid delivery pump 76 can be a squeeze pump that squeezes internal tubing 82 in a controlled manner, e.g., such as a peristaltic pump, to progressively move fluid from reservoir 78 to the distal end of catheter 74 and then into patient 6 according to parameters specified by a set of program information stored on memory 52 and executed by processor 50. Fluid delivery pump 76 can also be an axial pump, a centrifugal pump, a pusher plate, a piston-driven pump, or other means for moving fluid through internal tubing 82 and catheter 74. In one particular example, fluid delivery pump 76 can be an electromechanical pump that delivers fluid by the application of pressure generated by a piston that moves in the presence of a varying magnetic field and that is configured to draw fluid from reservoir 78 and pump the fluid through internal tubing 82 and catheter 74 to patient 6.

Periodically, fluid may need to be supplied percutaneously to reservoir 78 because all of a therapeutic agent has been or will be delivered to patient 6, or because a clinician wishes to replace an existing agent with a different agent or similar agent with different concentrations of therapeutic ingredients. Refill port 80 can therefore comprise a self-sealing membrane to prevent loss of therapeutic agent delivered to reservoir 78 via refill port 80. For example, after a percutaneous delivery system, e.g., a hypodermic needle, penetrates the membrane of refill port 80, the membrane may seal shut when the needle is removed from refill port 80.

Figure 15:
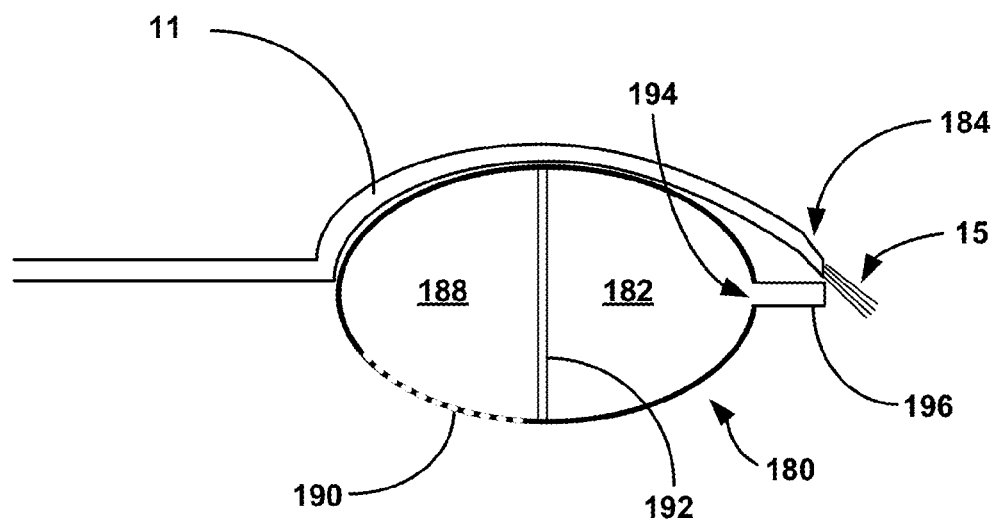
FIG. 15 is a conceptual diagram showing an osmotic pump used for delivery of a therapeutic agent.

In another example, shown in FIG. 15, a small pump 180 and fluid reservoir 182 may be located proximate a distal end 184 of a delivery device, such as an optical fiber 11, rather than within IMD 72, as shown schematically in FIG. 15. In one example, optical fiber 11 and pump 180 are implantable proximate the target tissue so that light 15 emitted from optical fiber 11 is substantially aligned with the target tissue adjacent to an output tube 196 of pump 180. This alignment allows light 15 to be directed to the same target tissue that is being transfected by the therapeutic agent. Pump 180 may be carried on another delivery device, such as a catheter or lead. In one example, pump 180 comprises a small fluid reservoir 182 containing the therapeutic agent (e.g., transfecting agent) that is to be delivered to the target tissue. Pump 180 may be an osmotic pump that utilizes the principles of osmosis to force fluid from reservoir 182.

Osmosis is the transfer of a solvent, e.g., water, across a barrier, generally from an area of lesser solute concentration to an area of greater solute concentration. In one example, osmotic pump 180 may be adapted to cause fluid to flow from the patient's surrounding tissue into a small compartment 188 through a semi-permeable membrane 190. This ingress of fluid into compartment 188, in turn, displaces a barrier 192 located between compartment 188 and the adjacent reservoir 182 containing the therapeutic agent. Displacement of barrier 192 forces the therapeutic agent from reservoir 182 into the patient's body at a controlled rate, for example through an opening 194 in reservoir 182 and/or through a delivery outlet tube 196. Delivery may occur after reservoir 182 is immersed in the body fluid. The rate of delivery may be controlled, for example, by selection of dimensions of compartment 188 and fluid reservoir 182, the flexibility and dimension of displaceable barrier 192, the size of opening 194 from fluid reservoir 182, the construction of permeable membrane 190, and/or the environment within compartment 188 into which the body fluid flows. Descriptions of osmotic pumps may be found in commonly assigned U.S. Patent Application Publication Nos.

2009/0281528 and 2008/0102119 entitled "Osmotic Pump Apparatus and Associated Methods," both of which are incorporated herein by reference in their entirety.

In some cases, use of osmotic pump 180 and associated reservoir 182 located at distal end 184 of a delivery device such as optical fiber 11 may have advantages over pumps and reservoirs located within IMD 72. For instance, the volume of tissue transfected by the therapeutic agent may be small. Likewise, the volume of tissue receiving an adequate amount of light 15 may also be small. By implanting a pump that is attached to the distal end 184 of the delivery device, such as optical fiber 11, allows for the alignment of these two small volumes such that the desired target tissue is transfected by the therapeutic agent and is exposed to an adequate amount of light 15, e.g. in order to activate the transfected target tissue.

Referring again to FIG. 5, at various times during the operation of IMD 72 to treat patient 6, communication to and from IMD 72 may be necessary to, e.g., change therapy programs, adjust parameters within one or more programs, configure or adjust a particular bolus, send or receive an estimated length of catheter 74, or to otherwise download information to or from IMD 72. Processor 50 therefore controls telemetry module 56 to wirelessly communicate between IMD 72 and other devices including, e.g. programmer 40. Telemetry module 56 in IMD 72, as well as telemetry modules in other devices described in this disclosure, such as programmer 40, can be configured to use RF communication techniques to wirelessly send and receive information to and from other devices respectively. In addition, telemetry module 56 may communicate with programmer 40 via proximal inductive interaction between IMD 72 and the external programmer. Telemetry module 56 may send information to external programmer 40 on a continuous basis, at periodic intervals, or upon request from the programmer.

Figure 12:
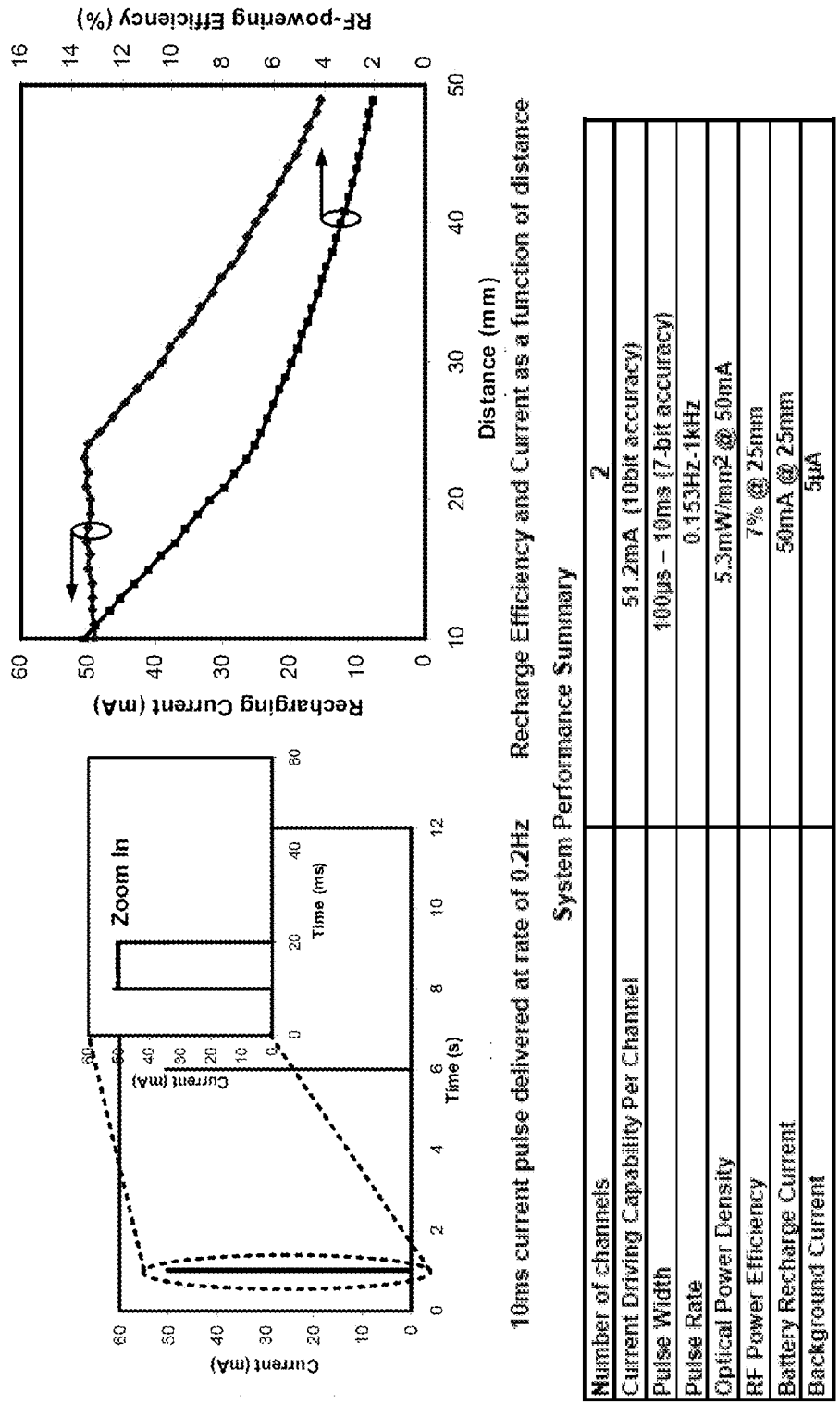
FIG. 12 is a characterization of measurement results of the example optogenetic neuromodulation system of FIG. 9.

Power source 54 delivers operating power to various components of IMD 72. Power source 54 may include a small rechargeable or non-rechargeable battery and a power generation circuit to produce the operating power. In the case of a rechargeable battery, recharging may be accomplished through proximal inductive interaction between an external charger and an inductive charging coil within IMD 72. In some examples, power requirements may be small enough to allow IMD 72 to utilize patient motion and implement a kinetic energy-scavenging device to trickle charge a rechargeable battery. In other examples, traditional batteries may be used for a limited period of time. As another alternative, an external inductive power supply could transcutaneously power IMD 72 as needed or desired. Measurement results for an example optogenetic stimulator system are summarized in FIG. 12. The system was configured to produce a benchmark pulse train of 10 ms current pulse with an amplitude of 50 mA and a 5 s period, which after passing through the optical link between the light source and target tissue results in an optical power density of 5.3 mW/mm$^2$ at the tissue interface. This power density is adequate for optical activation or deactivation, such as to activate a channelrhodopsin-2 for neuron activation and halorhodopsin for neuron deactivation. FIG. 12 also shows that RF powering provides 50mA recharging current at a distance of 25 mm insuring a fast recharging capability for higher power designs relying on other opsin channels. Its efficiency is 7% at 25 mm, which is comparable to other inductively-powered neural systems.

The benchmarked system power, currently limited by the conversion efficiency of the LED devices, is approximately 400 µW assuming successful opsin transfection into chronic neural circuits and equivalent neuromodulation. This power level is comparable to current deep brain stimulation systems, while providing the advantages of genetically-targeted stimulation, MRI/EMI compatibility and enhanced modulation capabilities.

An optogenetic modulation system such as system 2 of FIG. 1 provides for closed-loop feedback of the optical stimulation being generated by stimulator 4. For example, a stimulation program may be initiated by processor 50 that causes optical stimulation generator 60 to activate a light source 63, such as an LED or laser, which exposes a target tissue, such as a neuron population within brain 16 of patient 6, to light 15. As described above, because optical stimulation of light 15 does not generate a large electrical amplitude within the target tissue, bioelectrical activity within the target tissue may be monitored and recorded by sense electrodes, such as the implanted sense electrodes 17 on leads 12A and 12B, or a housing sense electrode 13. Moreover, unlike with electronic stimulation wherein sensing substantially simultaneously with the delivery of an electrical stimulation pulse is impossible because of the masking effect of the large stimulation amplitude compared to the bioelectric activity of interest, the sensing of bioelectric activity that is provided by sense electrodes 13 and/or 17 can be performed continuously before, during, and after optical stimulation of the target tissue. The ability to perform substantially simultaneous sensing also allows for the elimination of circuitry that attempts to compensate for or remove the artifacts resulting from electrical stimulation, allowing for an implantable stimulator with a smaller size that uses less power than electrical stimulators. This continuous and simultaneous sensing allows processor 50 or an external programmer, such as clinician programmer 20 or patient programmer 22, to not only record the effect of the performed optical stimulation, but also to provide a feedback loop that allows for adjustments to the treatment parameters of subsequent optical stimulations. In one example, the sense electrodes 13, 17 are used along with processor 50 to provide closed loop feedback based on sensed bioelectrical signals, such as single cell action potentials, local field potentials, energy spectra in different bands, such as alpha, beta, or gamma bands of brain activity, electrical signals associated with electrocorticography (ECoG) or electroencephalography (EEG). Further examples of sensing bioelectric signals substantially simultaneously with delivery of light for optical stimulation are provided in the co-pending application Ser. No. 12/951,852 entitled "Optical Stimulation Therapy," filed on the same date as the present application, which is assigned to the same assignee as the present application, the entire disclosure of which is incorporated herein by reference.

In one example, local field potentials (LFPs) may be used to sense neuronal activity in the brain continuously and substantially simultaneously with the delivery of optical stimulation. Low frequency power fluctuations of neuronal LFPs within discrete frequency bands can provide useful biomarkers for discriminating normal physiological brain activity from pathological states. LFPs may provide a measurement of the average or composite field behavior of many cells surrounding an electrode. Because LFPs represent the ensemble activity of thousands to millions of cells in an in vivo neural population, their recording may avoid chronic issues like tissue encapsulation and micromotion encountered in single-unit recording. LFP biomarkers are ubiquitous and span a broad frequency spectrum, from approximately 1 Hz oscillations in deep sleep to greater than approximately 500 Hz "fast ripples" in the hippocampus, and show a wide Q variation. As an example, high gamma band power fluctuations in the motor cortex may signal motion intent. Example techniques for monitoring selective frequency bands of physiological signals, including LFPs, are described in commonly assigned U.S. Patent Application Publication No. 2009/0082691 to Denison, entitled "Frequency Selective Monitoring of Physiological Signals," the entire disclosure of which is incorporated herein by reference.

Sensors may also be used to sense other biological parameters within the target tissue, such as inertial signals from an accelerometer, and pressure from a pressure sensor. After sensing a particular signal, processor 50 will run an algorithm and modulate the light provided to the target tissue appropriately. For example, sense electrodes 13, 17 may show that a particular optical stimulation program did not provide sufficient activation or inhibition of activity within the target tissue, i.e., the optical stimulation may not have activated the target neurons such that a neuronal spike was not created. Processor 50 may be programmed to recognize the result of the optical stimulation and to determine a subsequent course of action, such as to maintain the same treatment program because the present treatment was sufficient or to modify the treatment program because the present treatment was either insufficient or overly sufficient. For example, if processor 50 determines that the present treatment provided insufficient stimulation of the target tissue, such as the desired neural activation was not achieved in brain 16 of patient, processor 50 may instruct optical stimulation generator 60 to either repeat the same treatment program or to modify the treatment program, such as by providing more pulses, pulses with a different wavelength, pulses with a shorter or longer pulse width, or pulses with a higher or lower intensity, pulses delivered in longer or shorter bursts or at higher or lower burst frequencies. If the repeated or modified optical stimulation treatment is still insufficient, then processor 50 may be programmed to determine that the target tissue is no longer responsive to light 15 because the desired opsins are no longer being expressed and to instruct fluid delivery pump 76 to deliver additional therapeutic agent, such as a gene therapy agent, to promote expression of the opsins of interest in the target tissue. Either immediately thereafter or after some programmably-selected delay, processor 50 may then instruct optical stimulation generator 60 to provide another round of optical stimulation to determine if the therapeutic agent was effective in promoting optical stimulation of the target tissue. In another example, sense electrodes are used to detect electrical signals or other parameters within the target tissue in order to predict certain outcomes such that processor 50 may direct optical stimulation to encourage, inhibit, abort, or prevent the outcome. For example, sense electrodes may be used to detect the start of a seizure and processor 50 may respond by initiating optical stimulation to attempt to abort the seizure, or sense electrodes may be used to predict an oncoming seizure so that optical stimulation may be used to prevent the seizure. The sense electrodes may also be used to determine if the optical stimulation has inhibited or aborted the seizure, such as by monitoring the beta band of brain activity to determine if the patient is in a therapeutically beneficial state compared to before the optical stimulation. If the optical stimulation has aborted the seizure, processor 50 may instruct that optical stimulation be ceased. If the optical stimulation was unable to inhibit or cease the seizure, processor 50 may alter the treatment program, such as by increasing light intensity, changing pulse parameters (such as pulse width, pulse rate), changing pulse type (i.e. regular pulses versus pulse bursts), changing the optical fibers used in the optical stimulation, such as by using a different set of optical fibers or a different number of optical fibers. In another example, sense electrodes may be used to measure beta bands of brain activity to modulate optical stimulation for movement disorder therapy. In another example, a posture sensor such as an accelerometer may be used for posture responsive stimulation associated with spinal cord stimulation.

In another example, optical stimulation may be controlled based on a determination of whether a patient is in a movement state based on a brain signal of the patient. The brain signal may include a bioelectrical signal, such as an electroencephalogram (EEG) signal, an electrocorticogram (ECoG) signal, a signal generated from measured local field potentials (LFPs) within one or more regions of a patient's brain and/or action potentials from single cells within the patient's brain. In some examples, the brain signal may be detected within a dorsal-lateral prefrontal (DLPF) cortex of the patient's brain. The movement state includes the state in which the patient is generating thoughts of movement (i.e., is intending to move), initiating movement, attempting to initiate movement or is actually undergoing movement. In order to determine whether the bioelectrical signal indicates the patient is in a movement state or a rest state, the bioelectrical signal may be analyzed for comparison of a voltage or amplitude value with a stored value, temporal or frequency correlation with a template signal, a particular power level within a particular frequency band of the bioelectrical signal, or combinations thereof. In one example, a processor of a bioelectrical sensing device may monitor the power level of the mu rhythm within an alpha frequency band (e.g., about 5 Hertz (Hz) to about 10 Hz) of an EEG signal. If the power level of the mu rhythm falls below a particular threshold, which may be determined during a trial period, the EEG signal may indicate the patient is in a movement state. Other biomarkers in other spectral bands may be used, such as spectral power, amplitude, or other characteristics of signals in the alpha, beta, gamma, or high gamma bands. The sensing device may then control a therapy device to deliver optical stimulation to the patient to mitigate the effects of a movement disorder. For example, the sensing device may generate a control signal that is transmitted to the therapy device and causes the therapy device to initiate optical stimulation delivery or adjust one or more parameters of the optical stimulation. In some examples, the therapy systems and methods also include deactivating the delivery of therapy or changing therapy parameters upon determining the patient is in the rest state (i.e., as stopped moving) or has successfully initiated movement, depending upon the type of movement disorder symptom the therapy system is implemented to address. In addition, in some examples, a first determination that the patient is in a movement stated based on brain signals may be confirmed by a second determination that is based on another source that is independent of the brain signals, such as a motion sensor. Examples of the types of signals that may be sensed and how they may be interpreted are disclosed in the commonly-assigned U.S. patent application Ser. No. 12/237,799, which is entitled, "Therapy Control Based On A Patient Movement State," and was filed on Sep. 25, 2008, the disclosure of which is incorporated herein by reference in its entirety.

As discussed above, because optical fibers 11 are not electrically conducting, they do not provide a galvanic path for induced currents at the tissue interface so there is little to no risk of tissue capture or excessive heating that can occur due to gradient B fields or radio frequency (RF) fields, such as the fields associated with modalities such as magnetic resonance imaging (MRI) or electromagnetic interference (EMI). Moreover, the elimination of conductors from the tissue interface helps to mitigate MRI interference that is seen with typical electrical stimulation electrodes, allowing for continued high-resolution imaging post-implant. To retain these benefits provided by optical therapy delivery while also incorporating sensing capabilities into the system, in one example the structures that are proximate the target tissue, such as the sense electrodes, leads, fluid delivery structures, and optical fibers 11, are made from materials that produce substantially no induced current in an electromagnetic field, and in one example the structures proximate the target tissue produce substanatially no heating in gradient B fields or RF fields. For example, the sense electrodes and any leads carrying them may exhibit a very high resistivity and overall impedance so that they may be used to detect the types of signals discussed above, including LFPs, action potentials, and other biological signals. In some examples, such sensors have a high overall impedance (e.g., the cumulative impedance of the entire structure of sensor 154) of between about 100 Kiloohms and about 1 Megaohm. Examples of materials that may be used include a conductive polymer or a carbon fiber.

In one example, shown in FIG. 5, a high-impedance sensor 154 may be carried by an optical light guide, such as optical fiber 11, wherein sensor 154 is distributed along the length of optical fiber 11. Sensing is performed between high-impedance sensor 154 distributed along optical fiber 11 and a sensor on the housing of an implantable stimulator, such as housing sensor 13 on housing 14, wherein sensor 154 and housing sensor 13 are in a uni-polar mode. In example, sensor 154 may be formed of a material that produces substantially no induced current in an electromagnetic field, such as the fields created by MRI or EMI. In one example, sensor 154 has an overall impedance of between about 100 Kiloohms and about 1 Megaohm. In one example, sense electrode 154 does not comprise any material that will produce significant induced current and/or heating when exposed to an electromagnetic field, such as gradient B fields or RF fields, for example the fields created by MRI or EMI. Examples of materials that may be used for sensor 154 include a carbon fiber or a conductive polymer.

In one example, a sensor electrode 154 made from a conductive polymer or a carbon fiber is extruded over optical fiber 11 along the length of optical fiber 11, and a sheath (not shown), such as a polyether urethane sheath, is deposited over and surrounding the conductive polymer sensor 154. In one example, elongated sensor electrode 154 is formed of a conductive polymer or a carbon fiber, and a sheath is deposited over sensor 154, followed by extruding an optical fiber around the sheathed sensor 154. A high-impedance material is used because a current loop may be formed between sensor(s) 154, housing electrode 13, internal circuitry within housing 13, and any intervening tissue. If a lower inductance material were used in the present of a magnetic field such as the fields resulting from MRI or EMI, undesirable tissue capture or excessive heating may occur. In one example, the materials of each component, e.g., optical fiber 11, sensor 154, and the sheath, comprises a material that produce substantially no induced current and/or heating in an electromagnetic field, such as gradient B fields or RF fields. In one example, all structures that are proximate the target tissue, such as optical fiber 11, sensor 154, and the sheath, do not comprise any material that will produce significant induced current and/or heating when exposed to an electromagnetic field, such as gradient B fields or RF fields, for example the fields created by MRI or EMI.

The use of materials for optical fiber 11 and sensor 154 having a very high impedance that produce substantially no induced current and/or heating in an electromagnetic field is advantageous in a neurostimulation system such as those described herein. The lack of an induced current results in little to no risk of tissue capture or excessive heating, even from components that would traditionally do so, such as sense electrodes and the leads thereto. This, in turn allows MRI and other imaging technologies that may create electromagnetic fields, to be used substantially simultaneously with optical stimulation such that imaging and analysis of the patients tissue may be taken and performed at the time of stimulation. Moreover, the use of materials that do not produce induced current in an electromagnetic field from the tissue interface, such as the materials of optical fibers 11 and sensor 154, helps to mitigate MRI interference that is seen with typical electrical stimulation electrodes and sense electrodes, allowing for continued high-resolution imaging post-implant while still permitting for substantially simultaneous sensing during normal, day-to-day use of the optical stimulator.

In another example, housing electrode 13 is not used and need not be present, and sensing is performed between two sensors electrodes 156A, 156B which may be carried on the same optical fiber 11 (optical fiber 11B in FIG. 5), wherein sensing occurs in a bi-polar mode between sensors 156A and 156B. In one example, sensors 156A and 156B are positioned to extend along opposite diametrically opposed sides of optical fiber 11. Any current loop that might exists in such an arrangement would be created between the conductors of sensors 156A and 156B and the sensing circuitry 65 in housing 14 (FIG. 4). Sensing circuitry 65 may include a high impedance differential filter having an impedance on the order of about 1 Megaohm, and a differential amplifier that may filter out the common-mode signal from the two bi-polar sensed signals from sensors 156A, 156B. The high-impedance circuitry of sensing circuit 65 along with the small area between sensing conductors 156A and 156B due to their close positioning (only being spaced apart by optical fiber 11) results in very low magnetic flux that is less likely to induce large voltages. In some examples, sensors 156A, 156B have a high overall impedance (e.g., the cumulative impedance of the entire structure of each sensor 156A and 156B) of between about 100 Kiloohms and about 1 Megaohm. In one example, sensors 156A, 156B are made from a conductive polymer or a carbon fiber. In one example, in order to have enough physical spacing between the sense conductors 156A, 156B so that a sufficient differential signal may be detected, one of sensors 156A, 156B may extend further than the other, e.g., so that the distal ends of sensors 156A, 156B are spaced apart. For example, in FIG. 5, sensor 156A is shown as extending nearly to the distal end of optical fiber 11B, while sensor 156B terminates more proximal to the distal end of optical fiber 11B than sensor 156A.

Although optogenetic modulation systems have been described with respect to modification and stimulation of neuron populations, such as brain or spinal cord neurons, the present invention is not so limited. Optogenetic modulation systems in accordance with the present invention may be used for treatment of other target tissues, such as, for example, cardiac tissue, gastrointestinal tissue, and pelvic floor tissue. In one example, an optogenetic modulation system may be used for treatment of atrial fibrillation by providing ventricular rate control though modification of the atrio-ventricular (AV) node so that conduction to the ventricles during AF is slowed to within a desired physiological range.

In one example, stimulation of the AV node may include transfection of the AV node with a light-sensitive ion channel, such as a Kv1.3 potassium channel, a G-protein (Gi) channel, a leak channel with correct voltage and time dependence, and IKr or IKs channels, and implanting a stimulator similar to stimulator 4 or stimulator 34 described above that delivers light to the transfected AV node tissue. One or more sense electrodes may also be used to detect AF and enable optical stimulation of the AV node. In one example, a lead is placed in the right atrium appendage to detect AF while one or more optical fibers are positioned in the AV node to deliver light to the transfected tissue.

In another example, an optogenetic modulation system may provide for the suppression of AF triggers, such as triggers that originate in the pulmonary veins (PV) or the large vein ostia in the right atrium. AF triggers have been suppressed by using ablation to electrically isolate the trigger sites from the rest of the atrium. However, a disadvantage of ablation is that it irreversibly destroys tissue and may be associated with diminish atrial kick and compromised hemodynamics. Light-sensitive ion channels may be introduced to the PV ostia which, when triggered by optical stimulation, may depolarize the tissue to the extent that electrical activity from the focal triggers cannot travel to the rest of the atrium to trigger AF. In one example, the light-sensitive ion channel to suppress AF triggers may be a leak channel, such as a rhodopsin, that will provide for depolarization of the cell. In another example, atrial cells around the PV ostia may be transfected with a light-sensitive ion channel that could be optically stimulated with a generally circular light source or array of optical fibers when rapid triggered activity is detected in order to prevent initiation and/or sustenance of AF. In another example, optical stimulation may be provided in pulses with an appropriate duty cycle so that membrane potential is not hyperpolarized to stimulation levels.

In another example, an optogenetic modulation system may be used to suppress sympathetic activity associated with hypertension. In one example, light-sensitive ion channels that suppress this parasympathetic activity, such as leak channels or inwardly rectifying potassium channels, may be introduced to renal nerve cell bodies or sympathetic neurons in the lumbar region. Optical stimulation of these cells anchors the cell membranes to their resting potential and suppress the sympathetic activity. The optical stimulation may be performed on a substantially continuous basis or upon detection of elevated blood pressure, such as through the use of an implanted blood pressure sensor, for example a pressure sensor implanted in the RV outflow tract.

In yet another example, an optogenetic modulation system may be used to suppress errant biological pacemaker activity. Biological pacemakers have the potential to replace electronic pacemakers, however, the path to generating an effective biological pacemaker, including errant activity from the biological pacemaker that can cause undesired rapid firing of the biological pacemaker. A light-sensitive leak channel or IK1 channel, such as those encoded by Kir2.1 subunits, could be delivered at the same time as the biological pacemaker channels. Optical stimulation may be performed to activate the leak channels or IK1 channels and depolarize or hyperpolarize the cells so that rapid spontaneous activity by the biological pacemaker is either brought within the physiological range or stopped altogether. In another example, leak channels or IK1 channels may be introduced to the tissue encompassing the biological pacemaker so that upon optical stimulation the encompassing tissue can prevent rapid electrical activity of the biological pacemaker from propagating to the rest of the atria and ventricles.

In another example, optogenetic modulation system may be used to terminate or suppress ventricular tachycardia (VT). Prior methods that attempt to stop VT include anti-tachycardia pacing, such as with an implantable cardioverter-defibrillator, or with a shock across the heart. During VT, electrical activity in the atrium travels in a circuitous path, and is often rapid. This electrical activity can compromise ventricular hemodynamics and be fatal. In one example, light-sensitive channels may be introduced to a line of tissue upon detection of VT. Once optically stimulated, the VT circuit can be shifted to this functional line of tissue, which would be associated with a change in the morphology of the VT on a far-field electrocardiogram. Other means of monitoring whether the VT circuit has shifted may include measuring the electrical potential using a monophasic action potential (MAP) electrode located proximate the functional line of tissue. Once it is confirmed that the VT circuit has shifted to the functional line of tissue, the optical stimulation is ceased to deactivate the light-sensitive channels, thus making the myocardium excitable and terminating the VT. This optical treatment of VT would be painless, as compared to the generally painful electric shock necessary to terminate most VT.

Figure 16:
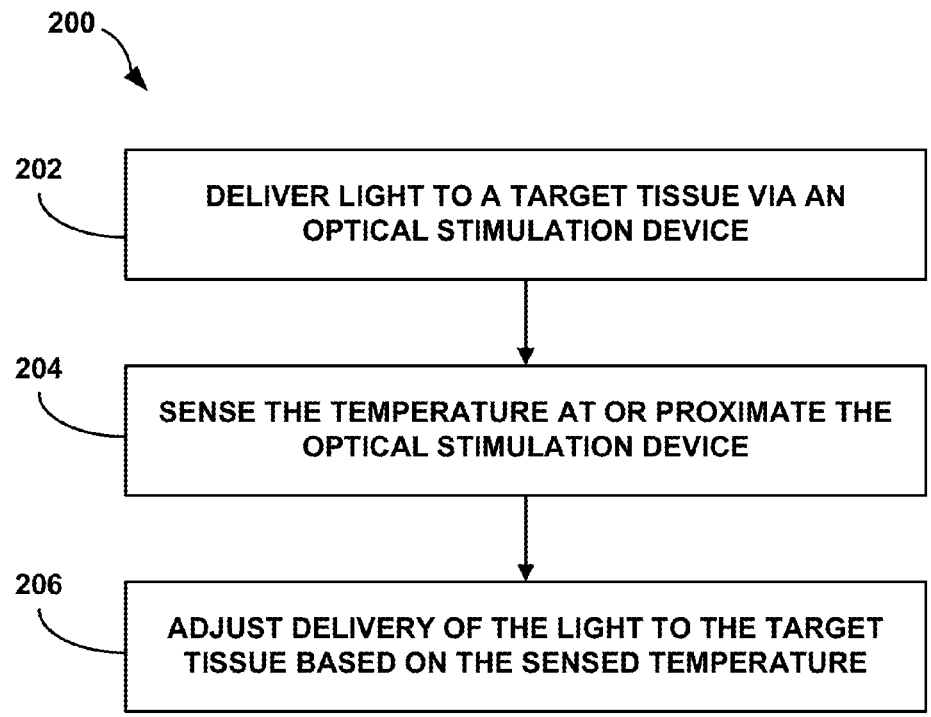
FIG. 16 is a flow diagram of an example method for delivering optical stimulation.

FIG. 16 is a flow diagram of an example method 200 for delivering optical stimulation. The example method 200 comprises delivering light to a target tissue via an optical stimulation device (202), such as from a light source of stimulators 4, 34, or 72 described above. During delivery of the light, a temperature at optical stimulation device 4, 34, 72 or proximate optical stimulation device 4, 34, 72 is sensed (204), and delivery of the light to the target tissue is adjusted based on the sensed temperature (206). Adjusting delivery of the light to the target tissue (206) may comprise reducing the power supplied to the light source, such as if the sensed temperature exceeds a threshold temperature, or adjusting at least one of a pulse rate of the light, a pulse width of the light, an amplitude intensity of the light, and a duty cycle of the light delivered by the light source. Adjusting delivery of the light (206) may also include ceasing delivery of the light, and if light delivery is ceased, optionally delivering electrical stimulation in place of the light stimulation.

Figure 17:
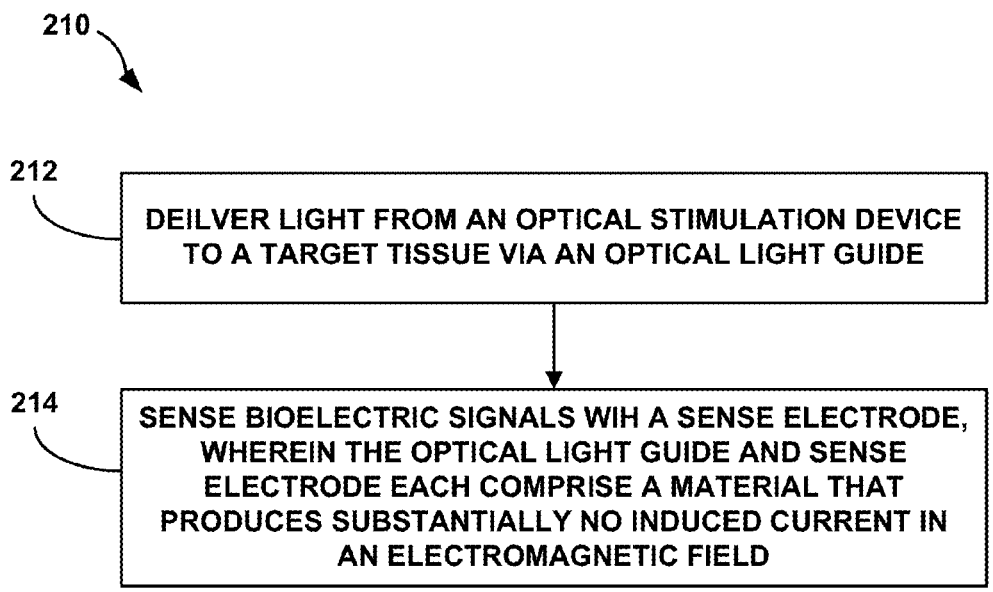
FIG. 17 is a flow diagram of another example method for delivering optical stimulation.

FIG. 17 is a flow diagram of an example method 210 for delivering optical stimulation. The example method 210 comprises delivering light from an optical stimulation device, such as simulator 4, 34, or 72, to a target tissue via an optical light guide, such as an optical fiber 11, wherein the optical stimulation device is remote from the target tissue (212). The method 210 also comprises sensing bioelectric signals with a sense electrode (214), such as sense electrodes 17, wherein optical light guide 11 and sense electrode 17 each comprise a material that produces substantially no induced current in an electromagnetic field, such as, for example, an electromagnetic field produced by a magnetic resonance imaging (MRI) device. In one example, the material of the sense electrodes and/or the optical fiber comprise at least one of a conductive polymer or a carbon fiber. In one example method, the sense electrode is on a lead, such as lead 12A, or 12B, and the lead is made from a material that produces substantially no induced current in an electromagnetic field.

Figure 18:
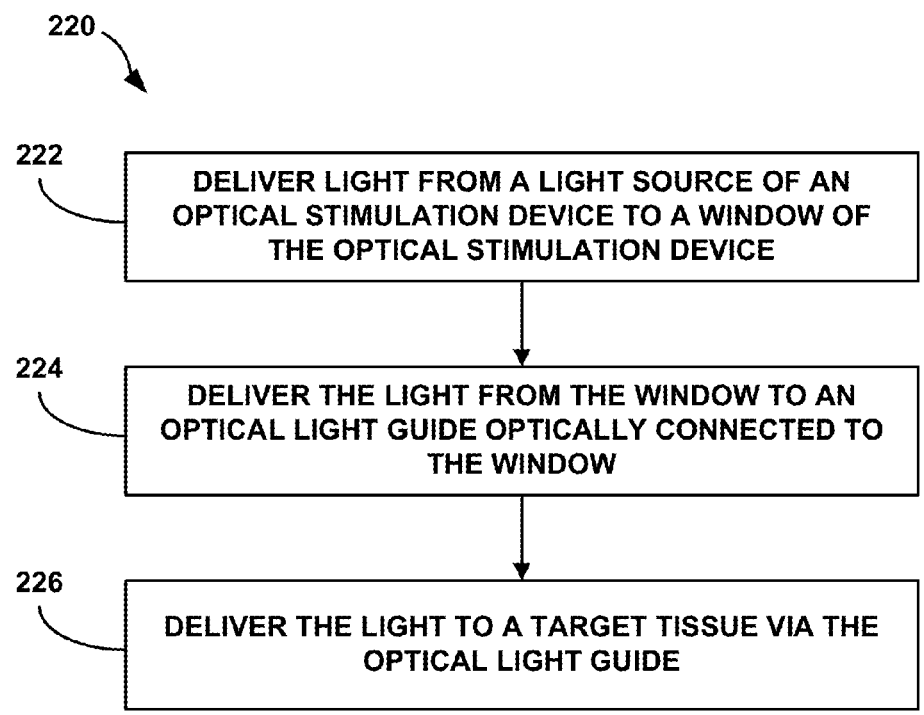
FIG. 18 is a flow diagram of another example method for delivering optical stimulation.

FIG. 18 is a flow diagram of an example method 220 for delivering optical stimulation. The example method 220 comprises delivering light from a light source of an optical stimulation device, such as LED 166 within stimulator 160 (FIG. 14), to a window 162 of optical stimulation device 160 (222), delivering the light from window 162 to an optical light guide, such as an optical fiber 11, optically connected to window 162 (224), and delivering the light to a target tissue via optical light guide 11 (226). Optical light guide 11 may be optically connected to window 162 via an optical index matching gel 170. Window 162 may be hermetically sealed within housing 164 of optical stimulation device 160. The example method may also include transfecting the target tissue with a light-sensitive channel protein sensitive to light in a wavelength range, wherein delivering light from light source 166 comprises delivering the light in the wavelength range, wherein delivering light from window 162 to optical light guide 11 comprises delivering the light in the wavelength range, and wherein delivering the light to the target tissue comprises delivering the light in the wavelength range.

Figure 19:
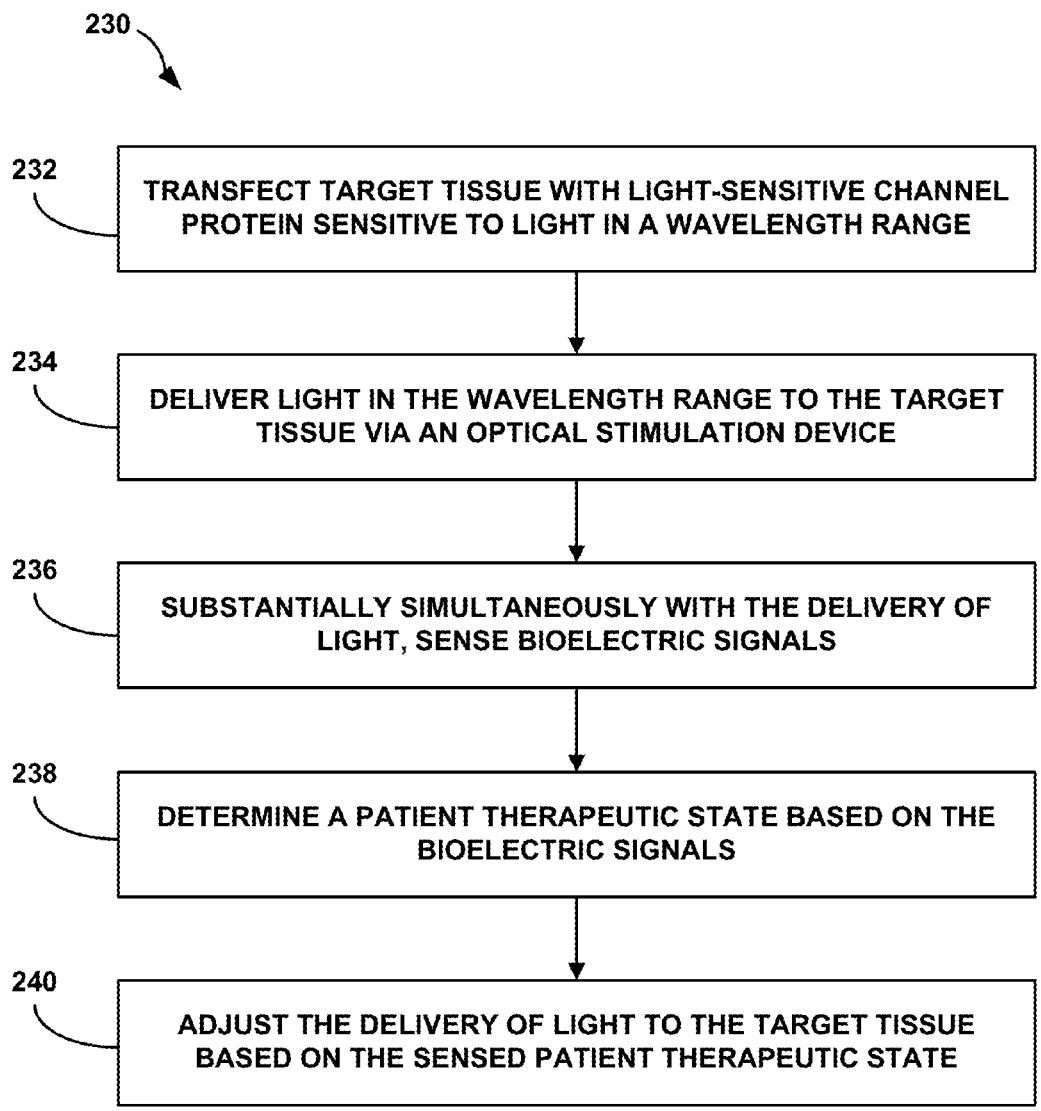
FIG. 19 is a flow diagram of another example method for delivering optical stimulation.

FIG. 19 is a flow diagram of an example method 230 for delivering optical stimulation. The example method 230 comprises transfecting a target tissue with a light-sensitive channel protein sensitive to light in a wavelength range (232) and delivering light in the wavelength range to the target tissue via an optical stimulation device (234). The example method 230 also comprises sensing bioelectric signals substantially simultaneously and continuously with delivering light to the target tissue (236), determining a patient therapeutic state based on the bioelectric signals (238), and adjusting delivery of the light to the target tissue based on the sensed patient therapeutic state (240).

Determining patient therapeutic state (238) may include determining whether the bioelectric signals indicate normal physiological activity of the target tissue, such as normal neural activity, or undesired activity, such as a pathological state. For example, the method may be used to provide closed-loop deep brain stimulation to treat movement disorders such as Parkinson's disease, spasticity, epilepsy, and dystonia. In some cases, the sensed bioelectric signals may result in a determination that the patient's therapeutic state indicates the onset of seizure, movement disorder symptoms, or other conditions. Upon such a determination, the method may trigger initiation or adjustment of optical stimulation to alleviate such symptoms. As an additional example, the method may be applied to support a cell-targeted treatment for schizophrenia, or for treatment of epilepsy via sensing and optical stimulation at various epileptic foci that provide distributed treatment of the epileptic foci.

Figure 20:
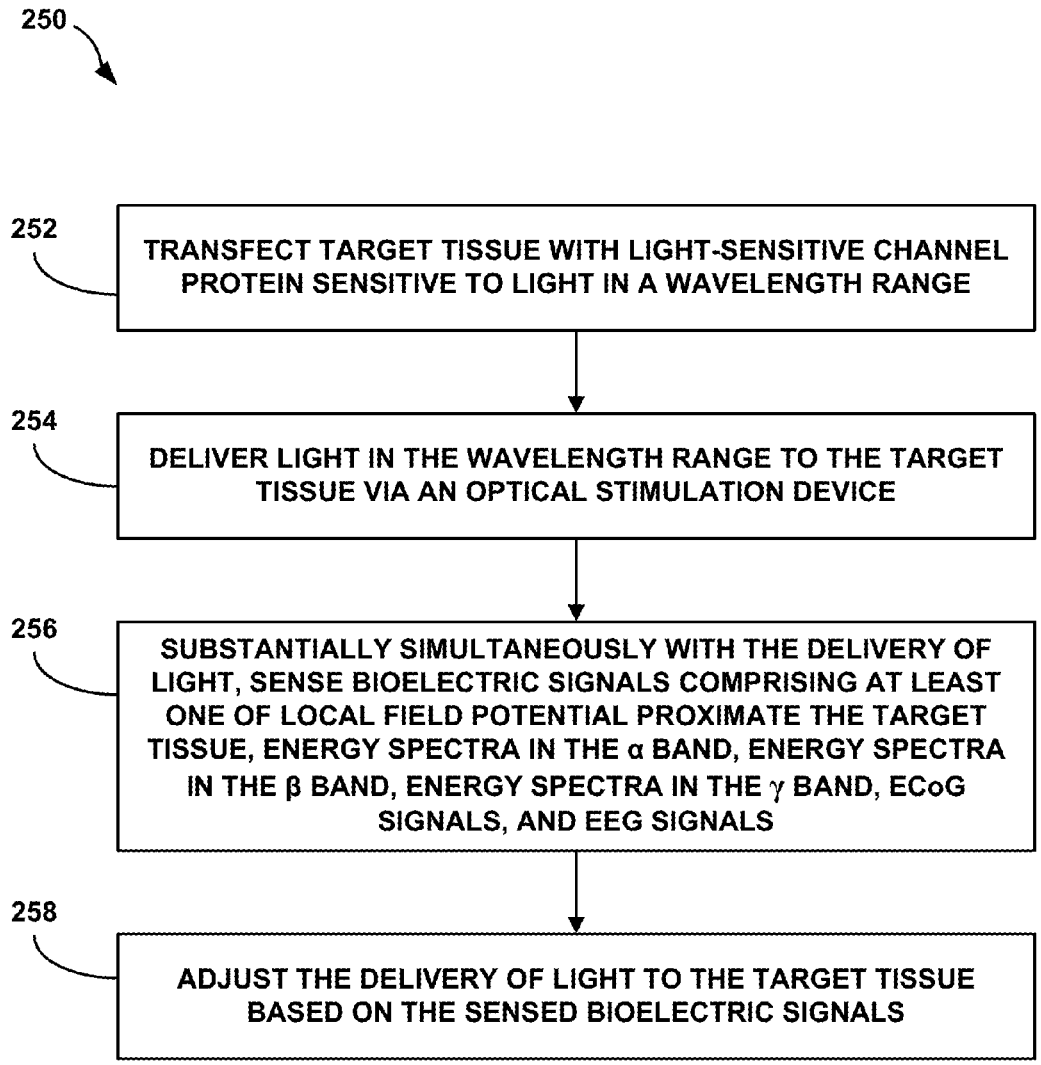
FIG. 20 is a flow diagram of another example method for delivering optical stimulation.

FIG. 20 is a flow diagram of another example method 250 for delivering optical stimulation. Like method 230 of FIG. 19, the example method 250 comprises transfecting a target tissue with a light-sensitive channel protein sensitive to light in a wavelength range (252) and delivering light in the wavelength range to the target tissue via an optical stimulation device (254). The example method 250 of FIG. 20 also comprises sensing bioelectric signals substantially simultaneously with delivering light to the target tissue (256), wherein the bioelectric signals comprises at least one of a local field potential proximate the target tissue, energy spectra in the alpha band of brain activity (α band), energy spectra in the beta band of brain activity (β band), energy spectra in the gamma band of brain activity (γ band), electrocorticography (ECoG) signals, and electroencephalography (EEG) signals. The example method 250 further comprises adjusting the delivery of light to the target tissue based on the sensed bioelectric signals (258).

Transfecting the target tissue (232, 252) and delivering light to the target tissue (234, 254) may be performed by a common implantable medical device, such as stimulator 4, 34, or 72. For example, stimulator 72 (FIGS. 5 and 6) comprises a reservoir 78 and fluid delivery pump 76 for the delivery of a therapeutic agent capable of trasnfecting the target tissue, and an optical stimulation generator 60, which may include a light source 63 (FIG. 3). A controller, such as processor 50, may control the output of light source 63 and may also direct the adjusting of light delivery (240, 258) based on the sensed bioelectric signals and/or patient therapeutic state.

Transfecting the target tissue (232, 252) may comprise delivering a therapeutic agent, such as a gene therapy agent, to the target tissue that transfects the target tissue, such as via a pump 76 from a reservoir 78 in optical stimulator 72 (FIG. 6) or using an osmotic pump 180 at a distal end 184 of a delivery device 186 (FIG. 14). Transfecting the target tissue (232, 252) may also comprise transfecting the target tissue with a first light-sensitive channel protein sensitive to light having a first wavelength range, for example an activating or exciting channel protein such as Channelrhodopsin-2 (described above), and transfecting the target tissue with a second light-sensitive channel protein sensitive to light having a second wavelength range, for example an inhibiting channel protein such as halorhodopsin (described above). If both the target tissue is transfected with both the first light-sensitive channel protein and the second light-sensitive channel protein, then delivering light to the target tissue (234, 254) comprises at least one of delivering light to the target tissue in the first wavelength range and delivering light to the target tissue in the second wavelength range.

Delivering light to the target tissue (234, 254) may comprise delivering light through an optical light guide, such as an optical fiber 11, optically coupled to the optical stimulation device, which may deliver the light from light source 63 to the target tissue. Delivering light to the target tissue (234, 254) may comprise delivering the light according to an optical stimulation program, such as a program configured for a particular patient condition or therapy. The optical stimulation program may include one or more optical stimulation parameters, such as a pulse rate of the light, a pulse width of the light, an amplitude intensity of the light, a duty cycle of the light, and a wavelength of the light. If an optical stimulation program is used, adjusting the delivery of the light to the target tissue (240, 258) may comprise adjusting the optical stimulation program, such as by adjusting at least one of the parameters (e.g., adjusting the pulse rate of the light, pulse width of the light, amplitude intensity of the light, duty cycle of the light, or wavelength of the light). Adjusting the delivery of light (240, 258) may also comprise adjusting the light substantially simultaneously with sensing the bioelectric signals (236, 256) and with delivering light to the target tissue (234, 254).

Sensing bioelectric signals (236, 256) may be provided by one or more sense electrodes on one or more leads, such as sense electrodes 17 on leads 12A, 12B (FIG. 1). A sensing module, such as sensing circuitry 65 controlled by processor 50, may be provided. In one example, sensing circuitry 65 is configured to sense and/or interpret bioelectric signals from sense electrodes 17 substantially simultaneously with the delivery of light from light source 63. In one example, processor 50 may be configured to determine a patient therapeutic state based on the bioelectric signals sensed by sense electrodes 17 and sensing circuitry 65.

Various examples have been described. These and other examples are within the scope of the following claims.

The invention claimed is:

1. A method for delivering optical stimulation, the method comprising:
   delivering light to a target tissue via an implanted optical stimulation device, wherein the implanted optical stimulation device comprises a therapy delivery module, the therapy delivery module comprising a light source and a controller that controls the light source to generate light;
   sensing a temperature at the optical stimulation device or proximate to the optical stimulation device via a temperature sensor;
   automatically ceasing, response to the temperature sensed by the temperature sensor rising above a threshold temperature, the delivery of light from the light source to the target tissue; and
   automatically delivering, in response to the temperature sensed by the temperature sensor rising above the threshold temperature, electrical stimulation to the target tissue via at least one electrical stimulation electrode while the delivery of light to the target tissue is ceased.

2. The method of claim 1, wherein ceasing the delivery of light from the light source to the target tissue comprises ceasing the power supplied to the light source.

3. The method of claim 1, wherein ceasing the delivery of light from the light source to the target tissue comprises reducing the power supplied to the light source.

4. The method of claim 3, wherein the threshold temperature comprises at least 2° C. over a selected body temperature.

5. The method of claim 1, further comprising reducing the delivery of light to the target tissue by at least adjusting at least one of a pulse rate of the light, a pulse width of the light, an amplitude intensity of the light, or a duty cycle of the light.

6. The method of claim 1, further comprising transfecting a target tissue with a light-sensitive channel protein sensitive to light in a wavelength range, wherein delivering light to the target tissue comprises delivering light in the wavelength range.

7. The method of claim 1, further comprising sensing bioelectric signals associated with the delivery of light to the target tissue.

8. The method of claim 1, further comprising initiating an alert in response to the temperature sensed by the temperature sensor rising above the threshold temperature.

9. A medical system comprising:
   an implantable stimulation device comprising a therapy delivery module, the therapy delivery module comprising a light source and a controller that controls the light source to generate light, and an electrical stimulation source, wherein the controller controls the electrical stimulation source to deliver electrical stimulation;
   an optical light guide configured to transmit the light from the light source to a target tissue;
   at least one electrical stimulation electrode implantable proximate the target tissue to deliver the electrical stimulation from the electrical stimulation source to the target tissue;
   a temperature sensor configured to sense a temperature of the implantable optical stimulation device or proximate the optical stimulation device,
   wherein the controller of the therapy delivery module is configured to, in response to the temperature sensed by the temperature sensor rising above a threshold level, automatically cease the delivery of light to the target tissue and automatically control the electrical stimulation source to deliver the electrical stimulation to the target tissue via the at least one electrical stimulation electrode while the delivery of light to the target tissue is ceased.

10. The medical system of claim 9, wherein the controller of the therapy delivery module is configured to cease the delivery of light by controlling at least one of power supplied to the light source, a pulse rate of the light transmitted from the light source, a pulse width of the light transmitted from the light source, or duty cycle of the light source.

11. The medical system of claim 9, wherein the controller of the therapy delivery module is configured to reduce power supplied to the light source when the sensed temperature rises above the threshold temperature.

12. The medical system of claim 11, wherein the threshold temperature comprises at least 2° C. over a selected body temperature.

13. The medical system of claim 9, wherein the therapy delivery module further comprises a fluid reservoir for storing a therapeutic agent.

14. The medical system of claim 9, further comprising a fluid delivery device configured to deliver a therapeutic agent, wherein the therapeutic agent transfects the target tissue with a light-sensitive channel protein sensitive to light in a wavelength range, wherein the light source is configured to deliver light in the wavelength range.

15. The medical system of claim 9, further comprising a sensing module configured to sense bioelectric signals associated with the delivery of light to the target tissue.

16. The medical system of claim 9, wherein the controller is configured to initiate an alert in response to the temperature sensed by the temperature sensor rising above the threshold temperature.

17. The medical system of claim 9, wherein the optical stimulation device comprises a housing enclosing the therapy delivery module.

18. The medical system of claim 17, wherein the housing encloses the temperature sensor.

19. The medical system of claim 17, wherein the temperature sensor is configured to sense the temperature of the optical stimulation device or proximate the optical stimulation device by at least sensing a temperature of the housing.

20. The medical system of claim 17, wherein the temperature sensor is configured to sense the temperature of the optical stimulation device or proximate the optical stimulation device by at least sensing a temperature outside the housing.

21. The medical system of claim 17, wherein the optical light guide is outside of the housing.

22. The medical system of claim 9, wherein the temperature sensor is configured to sense the temperature of the optical stimulation device or proximate the optical stimulation device by at least sensing a temperature of the light source.

23. The medical system of claim 9, wherein the controller of the therapy delivery module is configured to reduce the delivery of light to the target tissue by at least controlling the therapy delivery module to cease delivery of light to the target tissue.

\* \* \* \* \*

UNITED STATES PATENT AND TRADEMARK OFFICE
CERTIFICATE OF CORRECTION

Page 1 of 1

PATENT NO. : 8,936,630 B2
APPLICATION NO. : 12/951766
DATED : January 20, 2015
INVENTOR(S) : Denison et al.

It is certified that error appears in the above-identified patent and that said Letters Patent is hereby corrected as shown below:

In the Claims,

Col. 51, Line 28: "automatically ceasing, response to" should read --automatically ceasing, in response to--

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 5

<210> SEQ ID NO 1
<211> LENGTH: 310
<212> TYPE: PRT

<213> ORGANISM: Chlamydomonas reinhardtii

<400> SEQUENCE: 1

```
Met Asp Tyr Gly Gly Ala Leu Ser Ala Val Gly Arg Glu Leu Leu Phe
 1               5                  10                  15
Val Thr Asn Pro Val Val Asn Gly Ser Val Leu Val Pro Glu Asp
             20                  25                  30
Gln Cys Tyr Cys Ala Gly Trp Ile Glu Ser Arg Gly Thr Asn Gly Ala
             35                  40                  45
Gln Thr Ala Ser Asn Val Leu Gln Trp Leu Ala Ala Gly Phe Ser Ile
         50                  55                  60
Leu Leu Leu Met Phe Tyr Ala Tyr Gln Thr Trp Lys Ser Thr Cys Gly
 65                  70                  75                  80
Trp Glu Glu Ile Tyr Val Cys Ala Ile Glu Met Val Lys Val Ile Leu
                 85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Cys
            115                 120                 125
Pro Val Ile Leu Ile His Leu Ser Asn Leu Thr Gly Leu Ser Asn Asp
        130                 135                 140
Tyr Ser Arg Arg Thr Met Gly Leu Leu Val Ser Asp Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
        195                 200                 205
Arg Gln Val Val Thr Gly Met Ala Trp Leu Phe Phe Val Ser Trp Gly
        210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
        275                 280                 285
Ile Gly Gly Thr Glu Ile Glu Val Glu Thr Leu Val Glu Asp Glu Ala
    290                 295                 300
Glu Ala Gly Ala Val Pro
305                 310
```

<210> SEQ ID NO 2
<211> LENGTH: 930
<212> TYPE: DNA
<213> ORGANISM: Chlamydomonas reinhardtii

<400> SEQUENCE: 2

```
atggattatg gaggcgccct gagtgccgtt gggcgcgagc tgctatttgt aacgaaccca      60
gtagtcgtca atggctctgt acttgtgcct gaggaccagt gttactgcgc gggctggatt     120
gagtcgcgtg gcacaaacgg tgcccaaacg gcgtcgaacg tgctgcaatg gcttgctgct     180
ggcttctcca tcctactgct tatgttttac gcctaccaaa catggaagtc aacctgcggc     240
```

```
tgggaggaga tctatgtgtg cgctatcgag atggtcaagg tgattctcga gttcttcttc    300
gagtttaaga acccgtccat gctgtatcta gccacaggcc accgcgtcca gtggttgcgt    360
tacgccgagt ggcttctcac ctgcccggtc attctcattc acctgtcaaa cctgacgggc    420
ttgtccaacg actacagcag cgcaccatg gtctgcttg tgtctgatat ggcacaatt     480 gtgtggggcg ccacttccgc catggccacc ggatacgtca aggtcatctt cttctgcctg    540
ggtctgtgtt atggtgctaa cacgttcttt cacgctgcca aggcctacat cgagggttac    600
cacaccgtgc cgaagggccg tgtcgccag tggtgactg gcatggcttg gctcttcttc    660
gtatcatggg gtatgttccc catcctgttc atcctcggcc cgagggctt cggcgtcctg    720 agcgtgtacg gctccaccgt cggccacacc atcattgacc tgatgtcgaa gaactgctgg    780
ggtctgctcg ccactacct gcgcgtgctg atccacgagc atatcctcat ccacggcgac    840
attcgcaaga ccaccaaatt gaacattggt ggcactgaga ttgaggtcga cgctggtg     900 gaggacgagg ccgaggctgg cgcggtaccc                                     930

<210> SEQ ID NO 3
<211> LENGTH: 930
<212> TYPE: DNA
<213> ORGANISM: Chlamydomonas reinhardtii

<400> SEQUENCE: 3
atggactatg gcggcgcttt gtctgccgtc ggacgcgaac ttttgttcgt tactaatcct     60
gtggtggtga acgggtccgt cctggtccct gaggatcaat gttactgtgc cggatggatt    120
gaatctcgcg gcacgaacgg cgctcagacc gcgtcaaatg tcctgcagtg gcttgcagca    180
ggattcagca tttgctgct gatgttctat gcctaccaaa cctggaaatc tacatgcggc    240
tgggaggaga tctatgtgtg cgccattgaa atggttaagg tgattctcga gttcttttt     300 gagtttaaga atccctctat gctctaccct gccacaggac accgggtgca gtggctgcgc    360
tatgcagagt ggctgctcac ttgtcctgtc atccttatcc acctgagcaa cctcaccggc    420
ctgagcaacg actacagcag gagaaccatg ggactccttg tctcagacat cgggactatc    480
gtgtgggggg ctaccagcgc catggcaacc ggctatgtta aagtcatctt cttttgtctt    540
ggattgtgct atggcgcgaa cacattttt cacgccgcca aagcatatat cgagggttat    600
catactgtgc caaagggtcg tgtccgccag gtcgtgaccg gcatggcatg gctgttttc    660 gtgagctggg gtatgttccc aattctcttc attttggggc cgaaggtttt ggcgtcctg    720 agcgtctatg gctccaccgt aggtcacacg attattgatc tgatgagtaa aaattgttgg    780
gggttgttgg acactacct gcgcgtcctg atccacgagc acatattgat tcacggagat    840
atccgcaaaa ccaccaaact gaacatcggc ggaacggaga tcgaggtcga gactctcgtc    900
gaagacgaag ccgaggccgg agccgtgcca                                     930

<210> SEQ ID NO 4
<211> LENGTH: 308
<212> TYPE: PRT
<213> ORGANISM: Natronomonas pharaonis

<400> SEQUENCE: 4

Met Arg Gly Thr Pro Leu Leu Leu Val Val Ser Leu Phe Ser Leu Leu
 1               5                  10                  15

Gln Asp Thr Glu Thr Leu Pro Pro Val Thr Glu Ser Ala Val Ala Leu
            20                  25                  30
```

Gln Ala Glu Val Thr Gln Arg Glu Leu Phe Glu Phe Val Leu Asn Asp
                35                  40                  45

Pro Leu Leu Ala Ser Ser Leu Tyr Ile Asn Ile Ala Leu Ala Gly Leu
 50                  55                  60

Ser Ile Leu Leu Phe Val Phe Met Thr Arg Gly Leu Asp Asp Pro Arg
 65                  70                  75                  80

Ala Lys Leu Ile Ala Val Ser Thr Ile Leu Val Pro Val Val Ser Ile
                85                  90                  95

Ala Ser Tyr Thr Gly Leu Ala Ser Gly Leu Thr Ile Ser Val Leu Glu
                100                 105                 110

Met Pro Ala Gly His Phe Ala Glu Gly Ser Ser Val Met Leu Gly Gly
            115                 120                 125

Glu Glu Val Asp Gly Val Val Thr Met Trp Gly Arg Tyr Leu Thr Trp
130                 135                 140

Ala Leu Ser Thr Pro Met Ile Leu Leu Ala Leu Gly Leu Leu Ala Gly
145                 150                 155                 160

Ser Asn Ala Thr Lys Leu Phe Thr Ala Ile Thr Phe Asp Ile Ala Met
                165                 170                 175

Cys Val Thr Gly Leu Ala Ala Ala Leu Thr Thr Ser Ser His Leu Met
                180                 185                 190

Arg Trp Phe Trp Tyr Ala Ile Ser Cys Ala Cys Phe Leu Val Val Leu
            195                 200                 205

Tyr Ile Leu Leu Val Glu Trp Ala Gln Asp Ala Lys Ala Ala Gly Thr
210                 215                 220

Ala Asp Met Phe Asn Thr Leu Lys Leu Leu Thr Val Val Met Trp Leu
225                 230                 235                 240

Gly Tyr Pro Ile Val Trp Ala Leu Gly Val Glu Gly Ile Ala Val Leu
                245                 250                 255

Pro Val Gly Val Thr Ser Trp Gly Tyr Ser Phe Leu Asp Ile Val Ala
                260                 265                 270

Lys Tyr Ile Phe Ala Phe Leu Leu Leu Asn Tyr Leu Thr Ser Asn Glu
            275                 280                 285

Ser Val Val Ser Gly Ser Ile Leu Asp Val Pro Ser Ala Ser Gly Thr
290                 295                 300

Pro Ala Asp Asp
305

<210> SEQ ID NO 5
<211> LENGTH: 924
<212> TYPE: DNA
<213> ORGANISM: Natronomonas pharaonis

<400> SEQUENCE: 5
atgaggggta cgcccctgct cctcgtcgtc tctctgttct ctctgcttca ggacacagag    60
accctgcctc ccgtgaccga gagtgccgtg gcccttcaag ccgaggttac ccaagggag    120 ttgttcgagt tcgtgctgaa cgacccttg cttgcaagca gtctctatat caacatcgca    180
cttgcaggac tgagtatact gctgttcgtt tttatgaccc gaggactcga tgatccacgg    240
gcaaaactta ttgctgtgtc aaccatcctt gtgcctgtcg tcagcattgc ctcctacact    300
ggattggcga gcggcctgac aatttccgtt cttgaaatgc cagcgggcca ttttgcagaa    360
ggcagctcag tgatgctggg aggagaagag gtagatggtg tagtcaccat gtggggacgg    420
tatctcacct gggcactttc cacgcccatg attctcctcg ctctgggtct cctgccggga    480
agcaatgcta caaagctctt cacagctatc actttcgata tcgctatgtg cgtgactggc    540

```
cttgccgcgg ccctgactac ctcctcccac ctcatgagat ggttctggta cgctatcagt    600
tgtgcatgct ttctggtggt cttgtatatc ctgctggtgg agtgggcaca ggacgccaaa    660
gccgcgggaa ccgctgacat gttcaatacc ctgaagctgt tgacagtagt gatgtggctg    720
gggtatccaa ttgtgtgggc tcttggagtc gagggtatcg cggtgttgcc cgttggggtg    780
acgagctggg gatattcttt cctggatatc gtggcaaagt acattttcgc attcttgctc    840
ctgaactatc tgacgtcaaa cgaatctgtc gtgtccggca gcattttgga tgttccatct    900
gcttctggga ccccggctga tgat                                           924
```